(12) United States Patent
Miikkulainen et al.

(10) Patent No.: US 6,988,088 B1
(45) Date of Patent: Jan. 17, 2006

(54) SYSTEMS AND METHODS FOR ADAPTIVE MEDICAL DECISION SUPPORT

(75) Inventors: Risto Miikkulainen, Austin, TX (US); Michael D. Dahlin, Austin, TX (US); Randolph P. Lipscher, Austin, TX (US)

(73) Assignee: Recare, Inc., Austin, TX (US)

( * ) Notice: Subject to any disclaimer, the term of this patent is extended or adjusted under 35 U.S.C. 154(b) by 738 days.

(21) Appl. No.: 09/690,354

(22) Filed: Oct. 17, 2000

(51) Int. Cl.
  *G06F 15/18* (2006.01)
(52) U.S. Cl. .............................. 706/14; 706/15; 706/16
(58) Field of Classification Search .................. 706/14, 706/16, 15; 700/47, 48, 49
  See application file for complete search history.

(56) References Cited

U.S. PATENT DOCUMENTS

| | | |
|---|---|---|
| 4,839,822 A | 6/1989 | Dormond et al. |
| 4,858,121 A | 8/1989 | Barber et al. |
| 4,916,611 A | 4/1990 | Doyle, Jr. et al. |
| 5,018,067 A | 5/1991 | Mohlenbrock et al. |
| 5,065,315 A | 11/1991 | Garcia |
| 5,070,452 A | 12/1991 | Doyle, Jr. et al. |
| 5,072,383 A | 12/1991 | Brimm et al. |
| 5,077,666 A | 12/1991 | Brimm et al. |
| 5,101,476 A | 3/1992 | Kukla |
| 5,301,105 A | 4/1994 | Cummings, Jr. |
| 5,319,543 A | 6/1994 | Wilhelm |
| 5,347,453 A | 9/1994 | Maestre |
| 5,347,477 A | 9/1994 | Lee |
| 5,361,202 A | 11/1994 | Doue |
| 5,366,896 A | 11/1994 | Margrey et al. |
| 5,390,238 A | 2/1995 | Kirk et al. |
| 5,528,021 A | 6/1996 | Lassus et al. |
| 5,594,638 A | 1/1997 | Iliff |
| 5,660,176 A | 8/1997 | Iliff |
| 5,722,418 A | 3/1998 | Bro |
| 5,737,539 A | 4/1998 | Edelson et al. |

(Continued)

FOREIGN PATENT DOCUMENTS

WO    WO 2001/35376 A1    5/2001

(Continued)

OTHER PUBLICATIONS

Marian B. Gorzalczany et al. Computational intelligence in medical decision support- a comparison of two neuro-fuzzy systems Apr. 1999, IEEE, 0-7803-5662, 408-413.*

(Continued)

*Primary Examiner*—Anthony Knight
*Assistant Examiner*—Joseph P. Hirl
(74) *Attorney, Agent, or Firm*—John R. Schell; Toler, Larson & Abel, LLP

(57) ABSTRACT

The current invention is directed to a system for adaptive medical decision support. The invented system provides a system that allows users to efficiently enter, access, and analyze medical information, without disrupting patient-doctor interactions or medical facility course of business; which assists in all stages of medical assessment and treatment; and which is tailored to the particular medical practice or specialty and taking into account the developing habits, preferences, performance, and individual patient histories, of an individual user. The invention provides a learning capacity configured to learn previously presented data and decisions and predict data or decisions based on data that it receives from the user, thereby adapting its operations to the developing habits, preferences, performance, and individual patient histories of an individual user. The system may also provide a "virtual specialist" feature, whereby the system can be instructed to produce the probable actions or recommendations of particular medical specialists.

53 Claims, 12 Drawing Sheets

U.S. PATENT DOCUMENTS

| | | |
|---|---|---|
| 5,748,907 A | 5/1998 | Crane |
| 5,769,074 A | 6/1998 | Barnhill et al. |
| 5,772,585 A | 6/1998 | Lavin et al. |
| 5,778,882 A | 7/1998 | Raymond et al. |
| 5,845,255 A | 12/1998 | Mayaud |
| 5,868,669 A * | 2/1999 | Iliff .............................. 600/300 |
| 5,879,163 A | 3/1999 | Brown et al. |
| 5,883,370 A | 3/1999 | Walker et al. |
| 5,924,074 A | 7/1999 | Evans |
| 5,946,646 A | 8/1999 | Schena et al. |
| 5,951,300 A | 9/1999 | Brown |
| 5,954,641 A | 9/1999 | Kehr et al. |
| 5,992,890 A | 11/1999 | Simcox |
| 6,018,713 A | 1/2000 | Coli et al. |
| 6,021,202 A | 2/2000 | Anderson et al. |
| 6,024,699 A | 2/2000 | Surwit et al. |
| 6,026,363 A | 2/2000 | Shepard |
| 6,047,259 A | 4/2000 | Campbell et al. |
| 6,055,333 A | 4/2000 | Guzik et al. |
| 6,073,097 A | 6/2000 | Gould et al. |
| 6,073,375 A | 6/2000 | Fant et al. |
| 6,085,752 A | 7/2000 | Kehr et al. |
| 6,090,044 A * | 7/2000 | Bishop et al. .............. 600/300 |
| 6,108,635 A * | 8/2000 | Herren et al. ................... 705/2 |
| 6,113,540 A | 9/2000 | Iliff |
| 6,132,218 A | 10/2000 | Benja-Athon |
| 6,209,095 B1 | 3/2001 | Anderson et al. |
| 6,248,063 B1 | 6/2001 | Barnhill et al. |
| 6,298,348 B1 | 10/2001 | Eldering |
| 6,317,789 B1 | 11/2001 | Rakavy et al. |
| 6,385,592 B1 | 5/2002 | Angles et al. |
| 6,609,200 B2 | 8/2003 | Anderson et al. |
| 6,678,669 B2 * | 1/2004 | Lapointe et al. ............... 706/15 |
| 6,850,252 B1 * | 2/2005 | Hoffberg .................... 715/716 |
| 2001/0023419 A1 * | 9/2001 | Lapointe et al. .............. 706/15 |
| 2001/0032099 A1 | 10/2001 | Joao |
| 2002/0049612 A1 | 4/2002 | Jaeger et al. |

FOREIGN PATENT DOCUMENTS

WO    WO 2001/133378 A    5/2001

OTHER PUBLICATIONS

Goralczany, M.B., et al., "Computational intelligence in medical decision support a comparison of two neuro-fuzzy systems", Industrial Electronics, pp. 408-413, vol. 1, 1999.

Gorzalczany, M.B.: Gradzki, P., Computational intelligence in medical decision support a comparison of two neuro-fuzzy systems, Industrial Electronics, 1999. ISIE '99. Proceedings of the IEEE International Symposium on, vol.: 1, 1999, Page(s): 408-413, vol. 1.

* cited by examiner

400

EXAMPLES OF INFORMATION TRANSMITTED BY USER TO HOST COMPUTER (401, 402)

| PATIENT DATA | CLINICAL DATA |
|---|---|
| 1) Name | Address | Phone No. | 1) Vital Information (e.g., height, weight, temperature, blood pressure) |
| 2) Social Security No. | Birthdate | |
| 3) Race/Ethnicity | 2) Chief Complaint(s) |
| 4) Medical History (e.g., prior illnesses, recent preventative tests/results, prior medical procedures/results, prior vaccinations, congenital defects) | 3) Other Complaint(s) |
| | 4) Physical Examination Findings |
| | 5) Patient Answers to Diagnostic Questions |
| 5) Allergies | 6) Laboratory Orders and Results |
| 6) Habits (e.g., smoking, toxic exposure, drugs/alcohol) | 7) Diagnoses |
| | 8) Treatment Orders |
| 7) Current and Prior Medications | 9) Prescription and Pharmacy Information and Instructions |
| 8) Emergency Contact Information | |
| | 10) Date of Visit and Follow-Up Recommendations |
| 9) Insurance Information | |
| 10) Employment Information | 11) Physician/Nurse/Med Tech/P.A. ID Information |
| | 12) Billing and Coding Decisions |

| EXAMPLES OF INFORMATION OUTPUT TO USER BY HOST COMPUTER |
|---|

1) <u>Patient Assessment Information</u>

Recommendations for questions, physical examination, and medical tests (bloodwork, imaging, etc.).

Patient medical history data.

Name and comments from any referring physician(s).

Common oversights that may be checked at physician discretion.

Pertinent medical information, such as journal articles and the like.

2) <u>Diagnosis Information</u>

Names and descriptions of one or more alternative potential diagnoses.

Recommendations for additional data (e.g., pertinent negatives) that would exclude some potential diagnoses.

Pertinent medical information, such as journal articles and the like.

3) <u>Treatment Order Information</u>

Alternative recommendations for medication types and brands.

Alternative recommendations for surgical or non-surgical procedures.

Alternative recommendations for behavior (bedrest) or diet modifications.

Pertinent medical information, such as journal articles and the like.

4) <u>Virtual Specialist Information</u>

Data pertinent to specific ailment or injury.

Probability of certain actions or recommendations that would be given by specialist.

"Meantime care" – sufficient care until in-person consultation with specialist can be done.

Administrative Specialists such as billing and coding specialists.

FIG. 5

| ReCare | Austin Clinic – Dr.R.Lipscher | WORK | Home |
|---|---|---|---|

| Patients | Schedule | Health Plans | Correspondence | Refills | Tests | Messages | Forms | Admin |
|---|---|---|---|---|---|---|---|---|

| HPI | PMH | PE | Dx | Rx | Lab Results | Orders | Narrative | Forms | Ref |
|---|---|---|---|---|---|---|---|---|---|

Chest Pain – HPI    ★ Hector Black    United Healthcare    ID: 143567

| | | ROS | |
|---|---|---|---|
| Substernal | Location | GEN: | Weakness |
| Pressure-like | Quality | HEENT: | – |
| No | Radiation | RESP: | – |
| Moderate | Severity | GI: | Abdominal Pain |
| Unchanging | Evolution of Severity | MUSK: | – |
| Exertion | Precipitates | SKIN: | – |
| Walking during | First Episode | NEURO: | – |
| Resting | Alleviates | GU MALE: | – |
| No other | Symptoms with Episode | HEM: | – |
| 4 years Since | Onset | ALL/IMM: | – |
| Innumerable | Episodes Since Onset | ENDO: | – |
| 1 per day in | Frequency | PSYCH: | – |
| Gradually | Started | OTHER: | – |

Possible Diagnoses

| | |
|---|---|
| Angina Pectoris | 342.5 |
| Duodenal Ulcer | 555 |
| GERD | 456.3 |
| Esophageal Spasm | 444 |
| Pleurisy | 453.6 |
| Pulmonary Infarction | 443.2 |

| Becoming less | Frequent Over Time |
| 3 minutes | Longest Episode |
| 1 minute | Shortest Episode |
| Weakness | Recently a Problem |

FIG. 9

SYSTEMS AND METHODS FOR ADAPTIVE MEDICAL DECISION SUPPORT

TECHNICAL FIELD OF THE INVENTION

The present invention relates generally to computer-implemented systems and methods for gathering and analyzing medical information. More specifically, the invention is directed to a system and method for gathering and analyzing medical information and adaptively supporting medical decision-making.

BACKGROUND OF THE INVENTION

As human populations continue to expand more rapidly than the number of medical professionals, medical professionals become more scarce. Thus, medical professionals have ever-increasing needs to more efficiently serve their growing patient numbers, while maintaining consistent levels of quality and accuracy for the medical care that they provide. Many medical professionals use electronic medical records systems (EMR systems) to aid their practices. EMR systems allow users to electronically record, access, and analyze medical information and treatment orders. EMR systems can streamline data gathering, can bring standardization to the storage and presentation of medical information, can provide consistent access to medical information, and have in some instances been shown to improve accuracy in diagnoses and treatment orders.

Though EMR systems bear some advantages, the systems do not always increase efficiency to degrees that merit the time and cost of building and implementing them. For instance, many such systems have only one or a few centralized points of access— terminals or other computing devices—at which data must be entered and received. Users must often collect data themselves and then enter it into the system, nearly doubling their work. These points of access must also be used to access data. While electronic access is typically faster than sorting through paper files, the data must often be accessed, printed or written, and then delivered or relayed to another medical professional or patient who is not present at the access point. Again, the advantage of the systems over paper methods is only slight, when weighed against the time and cost required to build and implement the systems.

Because of the inefficiencies involved with using centralized points of access, electronic medical systems have rarely been adopted, except for storage purposes. Thus, systems that might support medical professionals, or other users, with medical decision-making have been slow to develop. In the 1970's, systems began to develop, which attempted to integrate clinical decision support with electronic medical records, by flagging errors or symptoms and by suggesting questions, tests, diagnoses or treatments. But again, users could access the systems only after locating one of a certain few designated hardware devices. The user was required to enter information, wait for system suggestions, and then relay the information to others at remote locations. In medical practices, this often frustrated both the medical professional and the patient, by disrupting patient-doctor interactions and the fluid course of business within medical care facilities.

Over time, the systems have become more specialized. But, as expensive and time-consuming as these systems are to build, they are only made more cumbersome by tailoring them to meet the needs of individual users. Medical practitioners, for example, often practice in specialized fields, such as cardiology or pediatric surgery. General practitioners often serve specific patient populations. All practitioners would be helped by tailoring systems to account for the peculiarities of their particular medical field and the history of cases that they have served, while also integrating their individual habits or preferences for routine diagnostic methods, terminology, certain medication types or brands, etc., into the systems. Thus, the current systems are not nearly as efficient, helpful, accurate, or easy to use, as they could be, or as users need them to be.

Some inventions make efforts to make individual, highly-specialized tasks more efficient and precise. These systems often employ learning systems or artificially-intelligent systems to enhance medical services. However, the systems are directed toward specific tasks. Some are only useful only for diagnosing one certain type of cancer; or predicting only the probability of heart attack or stroke, based on probabilities and biochemical markers. Other systems provide data analysis and interpretation, to recommend diagnoses or predict treatment outcomes, based on analytical models. Though a bit more useful than traditional rule-based systems, these inventions still do not learn individual preferences, habits, and case histories of their users and do not serve more than their single specific tasks. Additionally, the systems do not assist in assessing patients. Rather, they operate from a patient record that is established solely by the treatment provider. Thus, their utilities are fundamentally tied to the accuracy of the judgment of the treatment provider. Finally, because of the complex technology and great specialization involved in these systems, they are often monetarily out-of-reach for all but the most successful medical practices, and can hardly be justified for any but the most specialized.

Additionally, medical professionals often benefit from the experience of other medical professionals via consultations, training, treatment guidelines, or supervision. As electronic medical systems are deployed, they will be in a position to both observe the decisions of medical professionals and to dispense guidance to medical professionals. However, current systems do not provide an automated way to base guidance given to one medical professional (such as a medical student or nurse) on the decisions and experience of other medical professionals (such as residents or attending physicians). What is needed, then, is a method and system that learns the decision patterns of individual and groups of medical professionals and uses those decision patterns to guide other medical professionals.

Hence, there is a great need in the medical community for a system that allows users to efficiently enter, access, and analyze medical information, without disrupting patient-doctor interactions or medical facility business; which assists in all stages of medical assessment and treatment; and which is tailored to the particular medical practice or specialty and taking into account the developing habits, preferences, performance, and individual patient histories, of an individual user.

SUMMARY

The current invention is directed to a computer-implemented method for adaptively supporting medical decisions of one or more users. The invented method first includes receiving data and predicting one or more medical decisions based on the data. Data may be received via a wireless communication means, such as infrared signals, radio signals, and pulse codes. The data may be received from the immediate user, from a user who is not the immediate user, from information computers on which data are stored, from medical devices, and from network ports. The method also includes displaying the predicted medical decision(s).

The method also includes receiving one or more user-decisions. Each user-decision may be a predicted medical decision or may not be a predicted medical decision. The method also includes learning to predict the at least one user-decision from the data received. Learning may comprise updating one or more learning modules chosen from a group consisting of behavioral models, rule-based algorithms, learning-based algorithms, or neural networks. Learning may further comprise customizing operations to at least one parameter, such as preferences of a user, habits of a user, medical specialties of a user, patient populations of a user, preferences of a group of users, habits of a group of users, medical specialties of a group of users, and patient populations of a group of users.

The method may also include, after the step of receiving user-decisions, executing the user-decisions. The method may also include automatically executing the predicted medical decisions, before user-decisions are received. Executing a decision may comprise changing the state of a computation or process or communicating with an entity external to the system in some manner such as storing the decision, altering a computer display, updating a diagnosis or finding, ordering a medication, ordering a laboratory test, ordering an imaging test, ordering a consultation, retrieving information, displaying an article, changing the control path of a task, asking the user a question, sending information to a user, controlling a medical device, and the like. In one embodiment, the steps of the invented method may provide a "virtual specialist" to a user, by providing information pertaining to at least one medical specialty to the at least one user.

The method may also include displaying an electronic medical chart graphical user interface.

The invented method may be implemented on at least one portable computing device. Alternatively, the method may be implemented on a host computer that receives data transmitted from one or more portable computing devices, which also receive and display output from the host computer.

One embodiment of the current invention includes receiving data and transmitting the data to one or more neural networks. One or more medical decisions are then predicted by the neural networks, and the predicted medical decisions are displayed. One or more user-decisions are then received from the user or users. Each user-decision may be a predicted medical decision or may not be a predicted medical decision. The method also includes learning to predict the user-decisions from the data received, by updating the neural networks.

Another embodiment of the current invention is directed to an instance in which the learning is based on the decisions of one or more first users who are not the immediate user or users. This embodiment includes receiving one or more first quantities of data and one or more user-decisions from one or more first users. The embodiment includes learning to predict the user-decisions from the first quantities of data received. The embodiment next includes receiving one or more second quantities of data, predicting one or more medical decisions, and displaying the predicted medical decisions. The embodiment includes receiving one or more second user-decisions, but not learning from them.

Another embodiment of the current invention is directed to using rule-based algorithms to make predictions while learning develops. This embodiment includes receiving a first quantity of data and using at least one rule-based algorithm to predict one or more first medical decisions. These first medical decisions are displayed. The embodiment then includes receiving one or more user-decisions from one or more first users. The method may include executing the user-decisions, after they are received. The embodiment then includes learning to predict the user-decisions from the data received. The embodiment may also include executing the first predicted medical decision, before receiving the user-decisions. The embodiment also includes receiving a second quantity of data and using one or more learning-based algorithms to predict one or more second medical decisions. One or more third medical decisions are also predicted by the one or more rule-based algorithms. The method then involves displaying the second predicted medical decisions, or the third predicted medical decisions, or both. Which decisions are displayed may be selected automatically by a computing device or by one or more users. The embodiment may also include automatically executing either the second or third predicted medical decisions, or both.

Users of the invention may include different classes of users such as medical doctors, nurses, nurse practitioners, residents, medical students, medical staff, administrative staff, technicians, patients, payors, pharmacy benefits managers, insurance companies, and consultants. In one embodiment of the method, decisions are predicted for a first user or group of users, via the predictive model of a second user or group of users who may be of a different class than the first user.

The current invention is also directed to a software program, embodied on a computer-readable medium, incorporating the invented method.

The current invention is also directed to a computer-based system for adaptively supporting medical decisions of one or more users. The system includes means for receiving data; means for predicting medical decisions; means for receiving at least one user-decision; display means; and means for learning to predict the at least one user-decision, from the data received. The system may comprise one or more portable computing devices, or it may comprise both a host computer and one or more portable computing devices. The portable computing devices may be linked or integrated with a medical instrument. Each computing device may communicate with the host computer via a wireless communication means consisting of radio signals, infrared signals, or pulse codes. The means for learning may comprise one or more learning modules selected from a group consisting of at least one behavioral model, at least one rule-based algorithm, at least one learning-based algorithm, and at least one neural network.

BRIEF DESCRIPTION OF THE DRAWINGS

FIG. 4 shows a table illustrating examples of patient data and medical data that may be transmitted to the Host Computer.

FIG. 5 shows a table illustrating examples of information that may be transmitted to users from the Host Computer.

FIG. 9 shows an example of an electronic medical chart graphical user interface that may be used in an embodiment of the current invention.

DETAILED DESCRIPTION

Figure 1:
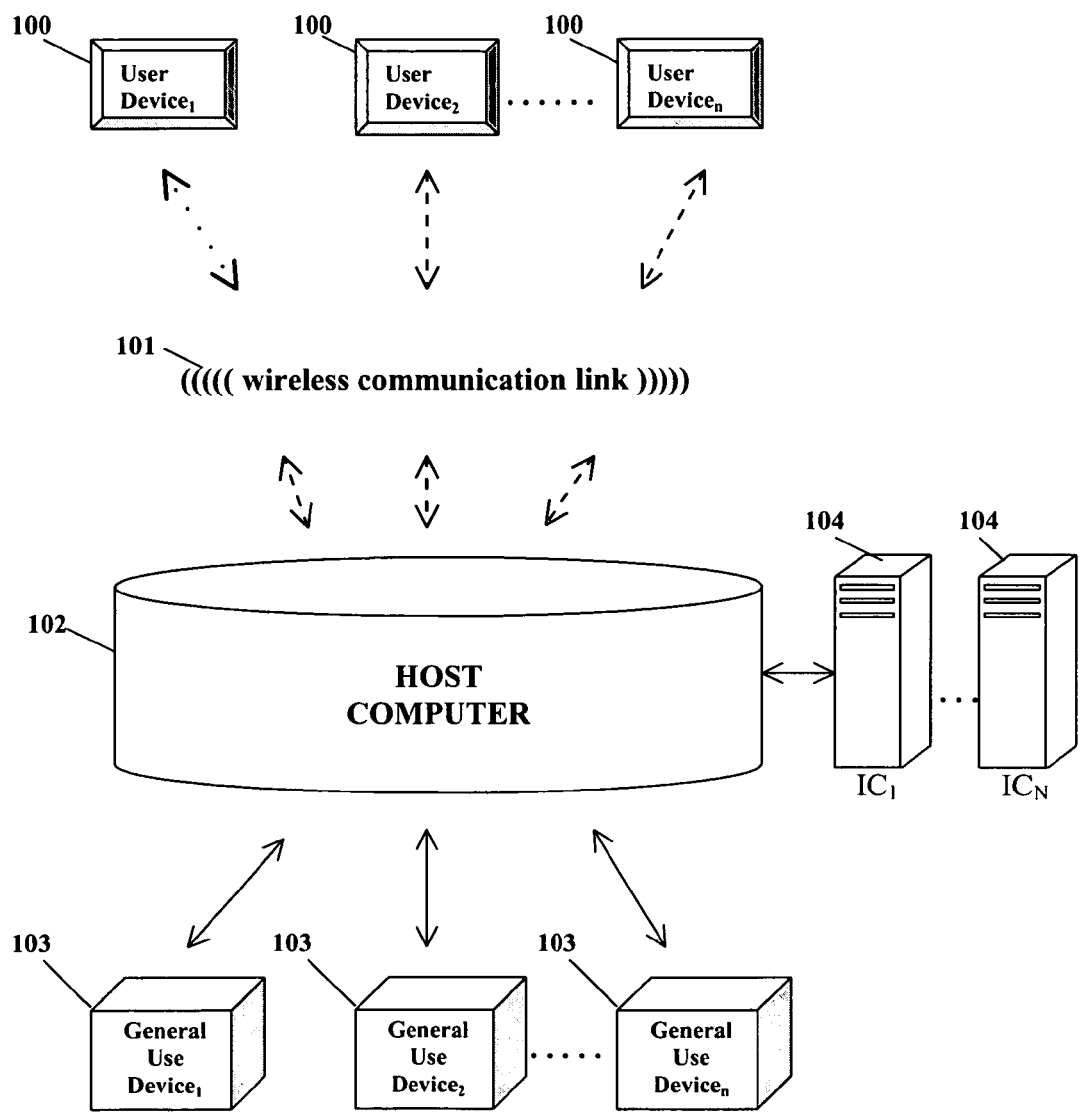
FIG. 1 shows a pictorial diagram, illustrating the components and steps of one embodiment of the currently invented method, in which at least one User Device and at least one general use device transmit and receive data with a Host Computer.

Referring now to the present invention, embodiments and examples of which are illustrated in the accompanying drawings, the current invention is directed to a system for adaptive medical decision support. Referring to FIG. 1, the system includes at least one User Device 100. These devices allow users to enter and receive medical data with a Host Computer 102. The User Device 100 comprises a portable computing device that is capable of communicating with other computing devices via a wireless communication link 101. The User Device 100 may comprise any portable computing device suitable for implementing the current invention, including a handheld wireless computing device, a wireless tablet form factor device, or a desktop or laptop computing device. The User Device 100 may also comprise a computing device linked or integrated with a medical instrument. The user interacts with the User Device 100 across a graphical user interface (GUI). In one embodiment of the invention, the GUI comprises an electronic medical chart interface that presents and organizes the data in the manner of paper medical charts, which are known to those in the medical field.

A user enters data via the User Device 100, which transmits the data via the wireless communication link 101 to the Host Computer 102. The data may comprise patient data, clinical data, or instructions to be executed by the Host Computer 102. The Host Computer 102 may be any computing device that is capable of receiving, transmitting, storing, and analyzing data, and executing operations. The Host Computer 102 may be a portable personal computer, a desktop personal computer, a handheld computing device that is capable of communicating remotely with other computers, or it may be a web server computer.

The wireless communication link 101 may comprise any technology suitable for relaying signals between a wireless computing device and a host computing device, without interference among separate wireless computing devices. This may include a number of wireless technologies that are well-known to those skilled in the art, including infrared signals, radio frequency signals, pulse codes, or frequency-diode modulation.

In one embodiment, one or more additional users may enter data via the User Devices 100, which transmit the data via the wireless communication link 101 to the Host Computer 102. This data may comprise patient data, clinical data, or instructions to be executed by the Host Computer 102. For example, a patient may enter data about his condition using a User Device 100 and those data are then transmitted to the Host Computer 102 via the wireless communication link 101. In another example, a medical technician or laboratory may enter data via a User Device 100, which transmit the data via the wireless communication link 101 to the Host Computer 102. This data may comprise the results of medical tests on a patient.

The Host Computer 102 may also retrieve additional data from computers that are external to the Host Computer 102. This data may comprise patient data, clinical data, or instructions to be executed by the Host Computer 102. In the embodiment shown in FIG. 1, the external computers comprise at least one Informational Computer 104.

The Host Computer 102 receives data and responds by executing operations and transmitting information. The Host Computer 102 may also store the data. In one embodiment, the data is stored on the Host Computer 102 in the form of an electronic chart. The data may also be stored on computers that are external to the Host Computer 102. In the embodiment shown in FIG. 1, the data is stored on Informational Computers 104, with which the Host Computer 102 communicates. The Host Computer 102 transmits information to the User Device 100 via wireless communication link 101. Examples of this information may include recommended diagnostic questions or tests that serve to reduce the probability of oversights during medical examination; past medical information for the patient; alternatives for diagnoses and treatment orders; and medical information, such as journal articles and the like. The Host Computer 102 may provide all relevant information and recommendations to the user, or only portions, and it may execute operations and provide information automatically or in conformity with user instructions.

Where the Host Computer 102 acts automatically, it does so by predicting decisions that the user, a separate user, or group of users will make during the course of treating each patient. These decisions may pertain to elements of medical examination, such as questions, findings, lab tests, clinical tests, or imaging; diagnosis and resulting treatment orders; and information that the user needs, such as patient history information, the opinions and recommendations of medical specialists or other medical professionals, similar cases that the user has served, and instructive information, such as journal articles and the like. Upon predicting user decisions, the Host Computer 102 forwards data pertaining to each decision that it has predicted. For example, in one embodiment, upon receiving data from the user, the Host Computer 102 may predict a certain diagnosis and then forward pertinent journal articles or suggested treatment orders to the user, to a separate user, or to a collection of users. In another embodiment, the Host Computer 102 may suggest diagnostic tests or questions that can eliminate potential oversights in the user's rendering of diagnoses or treatment orders.

Where the Host Computer 102 performs operations and forwards information according to user choice, the Host Computer 102 predicts the decisions that will be made by user and presents these decisions to the user by displaying them on the User Device 100. The user may select from the decisions predicted by the Host Computer 102, or enter alternatives. The Host Computer 102 then provides information or executes operations according to the user's input, which may comprise one or more of the predicted decisions or decisions that were not predicted. For example, in one embodiment, upon receiving patient or clinical data about a patient from the user, the Host Computer 102 may predict a certain diagnosis or range of diagnoses and display these to the user via the User Device 100. The user may then enter a selection, via the User Device 100, from among the diagnoses displayed. The user may also enter a diagnosis or range of diagnoses that are not displayed. Upon receiving the user's entry, the Host Computer 102 may then execute operations such as retrieving information such as journal articles, updating files, or suggesting treatment orders or further diagnostic tests or questions. The Host Computer 102 then displays resulting information to the user via the User Device 100.

The Host Computer 102 makes its predictions about a user's or a group of users' medical decisions, via a learning means that may execute behavioral models; rule-based algorithms, including rules, static lists, and decision support systems, such as MEDCIN; learning-based algorithms; neural networks; or any combination of these. In one embodiment, the Host Computer 102 utilizes a combination of rule-based algorithms and learning-based algorithms. In this embodiment, the Host Computer 102 maintains a behavioral model of the user to make its predictions of decisions that the user will make. During an initial period of use, the behavioral model is essentially empty. Thus, the Host Computer 102 makes its predictions based on rule-based algorithms The behavioral model is updated, when data and decisions are received from the user. As the behavioral model becomes more developed, predictions may be made based on both rule-based algorithms and the learning-based behavioral model. The resulting information may be merged together, producing a single output, or the information of each type may be kept separate and made selectable by the user. The user then has the option to disable the rule-based algorithms, when the user determines that the behavioral model has progressed beyond them. Additionally, the learning means may be disabled by the user, such that the predictive capability remains, without updating.

In another embodiment, each operation performed by the Host Computer 102 may comprise a plurality of decision nodes. The Host Computer 102 may then employ a neural network at each decision node, for predicting the decision that will be made by a user at the decision node. The Host Computer 102 may be programmed to execute the decision that it predicts or the decision that is input by the user. The Host Computer 102 updates each neural network, after receiving data and actual decisions from the user.

Regardless of the embodiment of the learning means, the prediction process is thus adapted to the user, such that the Host Computer 102 will predict the decisions actually input by a user in one case, when similar data or combinations of data are received in another case. But, the predictive process may also be updated, by predictively customizing the operations to the user's habits and preferences, while taking into account the characteristics of the user's specialty and patient populations. For instance, by updating its learning module with user habits, preferences, etc., the Host Computer 102 can increase its ability to predict when the user is likely to consult the virtual specialist feature of the invention, what medications the user prefers to prescribe for various ailments, what tests or diagnoses, if any, are commonly or uniformly rendered among the user's patient populations, etc. Thus, in addition to better predicting diagnoses and pertinent information, the Host Computer 102 can tailor the details of all its operations to the user's habits and preferences.

Regardless of the algorithms or models employed by the learning means, the Host Computer 102 may update the learning means each time that data or decisions are received from the user. Alternatively, updating may occur in "batch form," whereby updating occurs after a set period, such as after each case is complete, after a pre-defined number of cases are complete, after a pre-defined time period elapses, or after a pre-defined amount of data or decisions are received from the user, or any combination of these.

The system also provides at least one General Use Device 103 for interacting with The Host Computer 102. The General Use Device 103 is a computing device that communicates with the Host Computer 102. The General Use Device 103 may be non-portable. The General Use Device 103 may be a terminal computer that is dedicated to the Host Computer 102. The communication link between the General Use Device 103 and the Host Computer 102 may be wireless or wired. This communication may comprise communication via a global network (such as Internet), a wide area network, or a local area network. In one embodiment, the General Use Device 103 comprises at least one desktop computer that is centrally-located in an environment employing the system (such as a hospital), and is used for interacting with the Host Computer 102, in circumstances where patient/medical professional relationships are not disrupted or must be disrupted. Examples of circumstances where relationships are not disrupted include maintenance of the system or software installation, or where "batch" entry or review of medical data is desired. Examples of circumstances in which relationships must be disrupted include cases that are especially difficult and that require an atypically lengthy amount of study and analysis.

The Host Computer 102 may retrieve some or all information that it transmits to the user from its own memory. The Host Computer 102 may also, or alternatively, retrieve information that it transmits to the user from computers that are external to the Host Computer 102. In the embodiment shown in FIG. 1, the Host Computer 102 retrieves information from at least one Informational Computer 104. Where multiple Informational Computers 104 are used, they may be geographically distributed. The Host Computer 102 may communicate with each Informational Computer 104, via any suitable means for communication among computing devices. This may include wired or wireless means and may include communication via global network, such as Internet, wide area network, or local area network. In one embodiment, each Informational Computer 104 is a server computer, with which the Host Computer 102 communicates across a network.

The Host Computer 102 may also retrieve some or all information that it transmits to the user from a User Device 100 or a General Use Device 103 used by a different user to enter medical information. In one embodiment, a patient enters medical information about his condition into one User Device 100 and this information is transmitted to the User Device 100 used by a medical doctor via the Host Computer 102.

Figure 2:
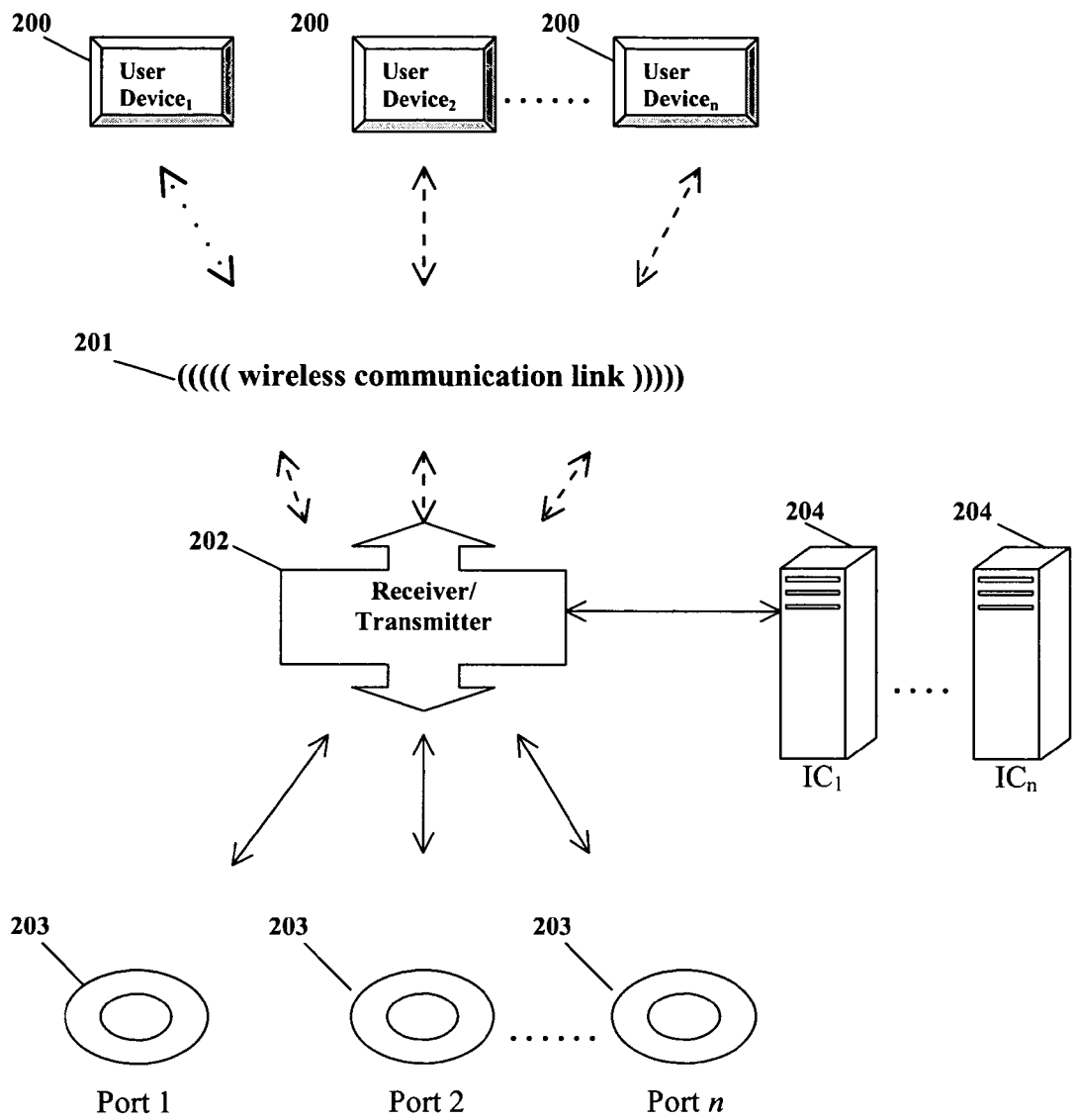
FIG. 2 shows a pictorial diagram, illustrating the components and steps of one embodiment of the currently invented method, in which each User Device performs the functions of the Host Computer.

Referring now to FIG. 2, the system includes at least one User Device 200. The User Device 200 comprises a portable computing device that is capable of communicating with other computing devices via a wireless communication link 201. The User Device 200 may comprise any portable computing device suitable for implementing the current invention, including those examples described with reference to FIG. 1. A user interacts with the User Device 200 across a graphical user interface (GUI). In one embodiment of the invention, the GUI comprises an electronic medical chart interface that presents and organizes the data in the manner of paper medical charts, which are known to those in the medical field.

A user enters data via the User Device 200. The data may comprise patient data, clinical data, or instructions to be executed by the User Device 200. The User Device 200 may store the data received from the user. In one embodiment, the data is stored in the form of an electronic chart, onto one or more Informational Computers 204, with which the User Device 200 communicates. In one embodiment, one or more additional users may enter data via the User Devices 200, which transmit the data via the wireless communication link 201 to other User Devices 200. This data may comprise patient data, clinical data, or instructions to be executed. For example, a patient may enter data about his condition using a User Device 200 and those data are then transmitted to the User Device 200 that is used by a medical professional or group of medical professionals. Similarly, a medical technician or laboratory may enter data via a User Device 200, which transmit the data via the wireless communication link 201 to a User Device 200 that is used by the medical professional or group of medical professionals. This data may comprise the results of medical tests on a patient.

The User Device 200 may also retrieve additional data from computers that are external to the User Device 200. This data may comprise patient data, clinical data, or instructions to be executed by the User Device 200. In the embodiment shown in FIG. 2, the external computers comprise at least one Informational Computer 204.

The User Device 200 responds to input data by executing operations and outputting information to the user. Examples of this information may include recommended diagnostic questions or tests that serve to reduce the probability of oversights during physical examination; past medical information for the patient; alternatives for diagnoses and treatment orders; and medical information, such as journal articles and the like. The User Device 200 may provide all relevant information and recommendations to the user, or only portions, and it may execute operations and provide information automatically or in conformity with user instructions.

Where the User Device 200 acts automatically, it does so by predicting decisions that the user will make during the course of treating each patient. These decisions may pertain to elements of physical examination, such as questions, lab tests, clinical tests, or imaging; diagnosis and resulting treatment orders; and information that the user needs, such as patient history information, the opinions and recommendations of medical specialists or other medical professionals, similar cases that the user has served, and instructive information, such as journal articles and the like. Upon predicting user decisions, the User Device 200 outputs data pertaining to each decision that it has predicted. For example, in one embodiment, upon receiving data from the user, the User Device 200 may predict a certain diagnosis and then forward pertinent journal articles or suggested treatment orders to the user. In another embodiment, the User Device 200 may suggest diagnostic tests or questions that can eliminate potential oversights in the user's rendering of diagnoses or treatment orders.

Where the User Device 200 performs operations and forwards information according to a user's choice, the User Device 200 predicts the medical decisions that will be made by a user and displays these predicted medical decisions to the user. The user may select from the decisions predicted by the User Device 200 or enter alternatives. The User Device 200 then provides information or executes operations according to the user's input, which may comprise one or more of the predicted decisions or decisions that were not predicted. For example, in one embodiment, upon receiving patient or clinical data about a patient from the user, the User Device 200 may predict a certain diagnosis or range of diagnoses and display these to the user. The user may then enter a selection, via the User Device 200, from among the diagnoses displayed, or the user may enter a diagnosis or range of diagnoses that are not displayed. Upon receiving the user's entry, the User Device 200 may then execute operations such as retrieving information including journal articles, updating files, or suggesting treatment orders or further diagnostic tests or questions. The User Device 200 then displays resulting information to the user.

The User Device 200 makes its predictions about a user's medical decisions, via a learning means that may execute behavioral models, rule-based or learning-based algorithms, and neural networks, in any of the manners described with reference to FIG. 1. In one embodiment, the User Device 200 utilizes a combination of rule-based algorithms and learning-based algorithms. In this embodiment, the User Device 200 maintains a behavioral model of the user to make its predictions of decisions that the user will make. During an initial period of use, the behavioral model is essentially empty. Thus, the User Device 200 makes its predictions based on rule-based algorithms The behavioral model is updated, when data and decisions are received from the user. As the behavioral model becomes more developed, predictions may be made based on both rule-based algorithms and the learning-based behavioral model. The resulting information may be merged together, producing a single output, or the information of each type may be kept separate and made selectable by the user. The user then has the option to disable the rule-based algorithms, when the user determines that the behavioral model has progressed beyond them. Additionally, the learning means may be disabled by the user instruction, such that the predictive capability remains, without updating.

Regardless of the embodiment of the learning means, the prediction process is thus adapted to the user, such that the User Device 200 will predict the decisions actually input by a user in one case, when similar data or combinations of data are received in another case. But, the predictive process may also be updated, by predictively customizing the operations to the user's habits and preferences, while taking into account the characters of the user's specialty and patient populations. For instance, by updating its learning module with user habits, preferences, etc., the User Device 200 can increase its ability to predict when the user is likely to consult the virtual specialist feature of the invention, what medications the user prefers to prescribe for various ailments, what tests or diagnoses, if any, are commonly or uniformly rendered among the user's patient populations, etc. Thus, in addition to better predicting diagnoses and pertinent information, the User Device 200 can tailor the details of all its operations to the user's habits and preferences.

No matter the algorithms or models employed by the learning means, the User Device 200 may update the learning means each time that data or decisions are received from the user. Alternatively, updating may occur in "batch form," whereby updating occurs after a set period, such as after each case is complete, after a pre-defined number of cases are complete, after a pre-defined time period elapses, or after a pre-defined amount of data or decisions are received from the user, or any combination of these.

The User Device 200 may retrieve some or all of the information it transmits to the user from its own memory, or from one or more external computers. In the embodiment shown in FIG. 2, the User Device 200 retrieves information from at least one Informational Computer (IC) 204, with which the User Device 200 communicates. The User Device 200 may communicate with each Informational Computer 204 via any suitable means for communication among computing devices. In the embodiment shown in FIG. 2, the User Device 200 communicates with each Informational Computer 204 by transmitting signals to the Receiver/Transmitter 202, via the wireless communication link 201. The signals are then transmitted to the Informational Computers 204. The Informational Computers 204 then return information to the Receiver/Transmitter 202, which sends signals back to the User Device 200.

The Receiver/Transmitter 202 may communicate with the Informational Computers 204, via a wireless communication link. Alternatively, the Receiver/Transmitter 205 may communicate with Informational Computers 204, via wired communication, such as a global network (such as the Internet), a wide area network, or a local area network. Alternatively, the Receiver/Transmitter 202 may be integrated or attached with at least one Informational Computer 204.

The wireless communication link 201 may comprise any technology suitable for relaying signals between a wireless computing device and a host computing device, without interference among separate wireless computing devices. This may include a number of wireless technologies, which are well-known to those skilled in the art, including infrared signals, radio frequency signals, pulse codes, or frequency-diode modulation.

The embodiment of the system shown in FIG. 2 also provides at least one Port 203. The User Device 200 may be "docked" at Ports 1 through n, i.e., connected to a wired network, to facilitate wired communication with the Informational Computers 204. This communication may comprise communication via a global network (such as Internet), a wide area network, or a local area network. Docking may be used, for example, for interacting with the Informational Computers 204 in circumstances where patient/medical professional relationships are not disrupted or must be disrupted. Examples of circumstances where relationships are not disrupted include maintenance of the system, software installation, or where "batch" entry or review of medical data is desired. An example of circumstances where the relationship must be disrupted includes a case that is especially difficult and requires an atypically lengthy amount of study and analysis. The User Device 200 may be connected at Ports 1 through n 203 by any means suitable for connecting a computing device to a docking port. These may include plugging one end of an electrical or optical cable into Port n 203 and the other end into a port or socket on the User Device 200.

Figure 3:
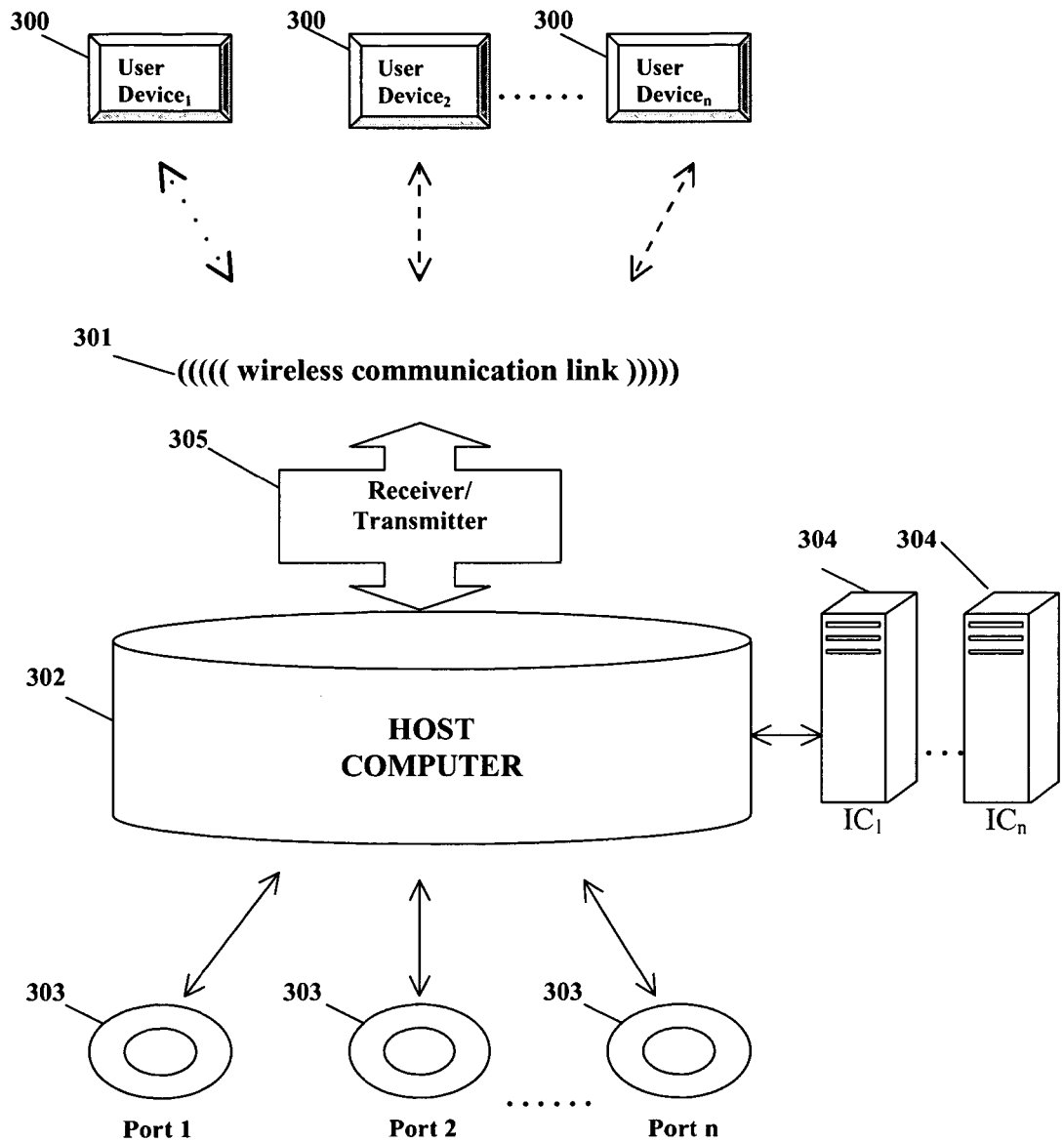
FIG. 3 shows a pictorial diagram, illustrating the components and steps of one embodiment of the currently invented method, in which a signal receiver/transmitter relays signals between the Host Computer and at least one User Device.

Now referring to FIG. 3, an alternative embodiment of the invented includes at least one User Device 300. The User Device 300 comprises a portable computing device that is capable of communicating with other computing devices via a wireless communication link. The User Device 300 may comprise any portable computing device suitable for implementing the current invention, including those examples described with reference to FIG. 1. The user interacts with the User Device 300 across a graphical user interface (GUI). In one embodiment of the invention, the GUI comprises an electronic medical chart interface that presents and organizes the data in the manner of paper medical charts, which are known to those in the medical field.

A user enters data via the User Device 300, which transmits the data via wireless communication link 301 to the Receiver/Transmitter 305. The data may comprise patient data, clinical data, or instructions to be executed by the Host Computer 302, such as particular information that the Host Computer 302 is to retrieve, analyze, or transmit. Receiver/Transmitter 305 relays signals that correspond to information and instructions, between the Host Computer 302 and each User Device 300. The Receiver/Transmitter 305 may be attached or integrated with the Host Computer 302, or it may communicate with the Host Computer 302 by remote means, such as wireless or network technologies. The Host Computer 302 may comprise any of the examples described with reference to FIG. 1.

In one embodiment, one or more additional users may enter data via the User Devices 300, which transmit the data via the wireless communication link 301 to the Host Computer 302. This data may comprise patient data, clinical data, or instructions to be executed by the Host Computer 302. For example, a patient may enter data about his condition using a User Device 300 and those data are then transmitted to the Host Computer 302 via the wireless communication link 301. For example, a medical technician or laboratory may enter data via a User Device 300, which transmit the data via the wireless communication link 301 to the Host Computer 302. This data may comprise the results of medical tests on a patient.

The Host Computer 302 may also retrieve additional data from computers that are external to the Host Computer 302. This data may comprise patient data, clinical data, or instructions to be executed by the Host Computer 302. In the embodiment shown in FIG. 3, the external computers comprise at least one Informational Computer 304.

Communication with the Receiver/Transmitter 305, by the Host Computer 302 and each User Device 300, may be achieved using any technology suitable for relaying signals between a wireless computing device and a signal receiver/transmitter, without interference among separate wireless computing devices. This may include a number of wireless technologies, the workings of which are well-known to those skilled in the art, including infrared signals, radio frequency signals, pulse codes, or frequency-diode modulation. In one embodiment of the invention, radio frequency signals are used to accomplish the wireless transmission of data from the wireless devices to a radio signal receiver/transmitter.

The system also provides at least one Port 303. The User Device 300 may be "docked" at Ports 1 through n, i.e., connected to a wired network, to facilitate wired communication with the Host Computer 302. This communication may comprise communication via global network (such as Internet), wide area network, or local area network. Docking is used for interacting with the Host Computer 302, in circumstances where patient/medical professional relationships are not disrupted or must be disrupted. Examples of circumstances where relationships are not disrupted include maintenance of the system, software installation, or where "batch" entry or review of medical data is desired. An example of circumstances where the relationship must be disrupted includes a case that is especially difficult and requires an atypically lengthy amount of study and analysis. The User Device 300 may be connected at Ports 1 through n, by any means suitable for connecting a computing device to a docking port. These may include plugging one end of an electrical or optical cable into Port n 303 and the other end into a port or socket on the User Device 300.

The Host Computer 302 receives data and responds by executing operations and transmitting information. The Host Computer 302 may store the data received from the user. In one embodiment, the data is stored in the form of an electronic chart, onto one or more Informational Computers 304, with which the Host Computer 302 communicates. The Host Computer 302 transmits information to the User Device 300 via a wireless communication link 301 and a Receiver/Transmitter 305. Examples of this information may include recommended diagnostic questions or tests that serve to reduce the probability of oversights during physical examination; past medical information for the patient; alternatives for diagnoses and treatment orders; and medical information, such as journal articles and the like. The Host Computer 302 may provide all relevant information and recommendations to the user, or only portions, and it may execute operations and provide information automatically or in conformity with user instructions.

Where the Host Computer 302 acts automatically, it does so by predicting decisions that the user will make during the course of treating each patient. These decisions may pertain to elements of physical examination, such as questions, lab tests, clinical tests, or imaging; diagnosis and resulting treatment orders; and information that the user needs, such as patient history information, the opinions and recommendations of medical specialists or other medical professionals, similar cases that the user has served, and instructive information, such as journal articles and the like. Upon predicting user decisions, the Host Computer 302 forwards data pertaining to each decision that it has predicted. For example, in one embodiment, upon receiving data from the user, the Host Computer 302 may predict a certain diagnosis and then forward pertinent journal articles or suggested treatment orders to the user. In another embodiment, the Host Computer 302 may suggest diagnostic tests or questions that can eliminate potential oversights in the user's rendering of diagnoses or treatment orders.

Where the Host Computer 302 performs operations and forwards information according to user choice, the Host Computer 302 predicts the decisions that will be made by user and presents these decisions to the user by displaying them on the User Device 300. The user may select from the decisions predicted by the Host Computer 302, or =enter alternatives. The Host Computer 302 then provides information or executes operations according to the user's input, which may comprise one or more of the predicted decisions or decisions that were not predicted. For example, in one embodiment, upon receiving patient or clinical data about a patient from the user, the Host Computer 302 may predict a certain diagnosis or range of diagnoses and display these to the user via the User Device 300. The user may then enter a selection, via the User Device 300, from among the diagnoses displayed, or the user may enter a diagnosis or range of diagnoses that are not displayed. Upon receiving the user's entry, the Host Computer 302 may then execute operations such as retrieving information such as journal articles, updating files, or suggesting treatment orders or further diagnostic tests or questions. The Host Computer 302 then displays resulting information to the user via the User Device 300.

The Host Computer 302 makes its predictions about a user's medical decisions, via a learning means that may execute behavioral models, rule-based or learning-based algorithms, and neural networks, or any combination of these, in any of the manners described with reference to FIG. 1.

In one embodiment, the Host Computer 302 utilizes a combination of rule-based algorithms and learning-based algorithms. In this embodiment, the Host Computer 302 maintains a behavioral model of the user to make its predictions of decisions that the user will make. During an initial period of use, the behavioral model is essentially empty. Thus, the Host Computer 302 makes its predictions based on rule-based algorithms The behavioral model is updated, when data and decisions are received from the user. As the behavioral model becomes more developed, predictions may be made bases on both rule-based algorithms and the learning-based behavioral model. The resulting information may be merged together, producing a single output, or the information of each type may be kept separate and made selectable by the user. The user then has the option to disable the rule-based algorithms, when the user determines that the behavioral model has progressed beyond them. Additionally, the learning means may be disabled by the user instruction, such that the predictive capability remains, without updating.

Regardless of the embodiment of the learning means, the prediction process is thus adapted to the user, such that the Host Computer 302 will predict the decisions actually input by a user in one case, when similar data or combinations of data are received in another case. The prediction process is thus adapted to the user, such that the Host Computer 302 will predict the decisions actually input by a user in one case, when similar data or combinations of data are received in another case. But, the predictive process may also be updated, by predictively customizing the operations to the user's habits and preferences, while taking into account the characters of the user's specialty and patient populations. For instance, by updating its learning module with habits, preferences, etc., of the user, the Host Computer 302 can increase its ability predict when the user is likely to consult the virtual specialist feature of the invention, what medications the user prefers to prescribe for various ailments, what tests or diagnoses, if any, are commonly or uniformly rendered among the user's patient populations, etc. Thus, in addition to better predicting diagnoses and pertinent information, the Host Computer 302 can tailor the details of all its operations to the user's habits and preferences.

Regardless of the algorithms or models employed by the learning means, the Host Computer 302 may update the learning means each time that data or decisions are received from the user. Alternatively, updating may occur in "batch form," whereby updating occurs after a set period, such as after each case is complete, after a pre-defined number of cases are complete, after a pre-defined time period elapses, or after a pre-defined amount of data or decisions are received from the user, or any combination of these. The Host Computer 302 may also update the learning means each time that the User Device 300 is docked at a Port n 303.

The Host Computer 302 may retrieve some or all of the information it transmits to the user from one or more Informational Computer (IC) 304, with which the Host Computer 302 communicates. The Host Computer 302 may communicate with each Informational Computer 304 via any suitable means for communication among computing devices. This may include wireless and wired means, and may include communication via a global network (such as Internet), a wide area network, or a local area network. In one embodiment, each Informational Computer 304 is a server computer, with which the Host Computer 302 communicates across a network.

FIG. 4 is a table 400 that displays examples of data that may be transmitted by a user to the Host Computer, via a User Device or a General Use Device, as described with the system above. The column at 401 shows examples of patient data that may be transmitted to the Host Computer. The column at 402 shows examples of clinical data that may be transmitted to the Host Computer. Examples of patient data 401 that may be transmitted to the Host Computer include a patient's name and personal contact information, name and contact information of one to contact in emergency, as well as social security number and birthdate. Patient data may also include, but is not limited to, information bearing upon medical diagnosis and treatment, such as ethnicity, medical history, Do-Not-Resuscitate (DNR) orders, allergies to drugs and other allergens, current and prior medications, and health habits, such as smoking, toxic exposure, and use of drugs or alcohol. Examples of patient data also include payment-related information, such as insurance information and employment data. The list in FIG. 4 is meant to be illustrative and not all inclusive. It will be appreciated that many other types of patient data may be transmitted also.

Examples of clinical data 402 that may be transmitted to the Host Computer include vital information, such as height, weight, body temperature, pulse rate, blood pressure, pulse oxygenation, blood type, blood pH, etc. Examples of medical data may also include data that is directly pertinent to diagnosing a medical problem, such as the patient's complaints and symptoms, physical examination findings and laboratory results, and the patient's answers to diagnostic questions. Example medical data may also include the medical professional's diagnosis and treatment orders. If medication is dispensed for treatment, the medical data may include prescription instructions and information, information and instructions for the dispensing pharmacy. Examples of medical data may also include the date of visit by the patient and any follow-up recommendations, and the name of the medical professional who served the patient on the date of visit. The list in FIG. 4 is means to be illustrative and not all inclusive. It will be appreciated that many other types of clinical data may be transmitted also.

FIG. 5 is a table 500 illustrating examples of information that may be output to a user by the Host Computer, as described with the system above, in order to provide medical decision support to the user. Examples of information pertaining to patient assessment that may be output by the Host Computer to the user include but are not limited to recommendations for diagnostic questions, physical examinations, and medical tests, such as blood tests or imaging (X-ray, MRI, CT, etc.); medical history data concerning the patient; the name(s) and comments of any referring medical personnel(s); alerts to common oversights in patient assessment, which may be checked at medical personnel discretion; and medical information, such as journal articles and the like.

Examples of information pertaining to diagnosis that may be output by the Host Computer to the user include but are not limited to names, or other identifying references, for potential diagnoses, along with a brief description of each diagnosis that is presented; recommendations for additional data (e.g., pertinent negatives) that would exclude one or more potential diagnoses; and medical information, such as journal articles and the like.

Examples of information pertaining to treatment orders that may be output by the Host Computer to the user include but are not limited to recommendations for treatment orders or alternative treatment orders, including presenting to the user alternative medication types and brands; alternative recommendations for surgical or non-surgical procedures; alternative recommendations for behavior modifications (e.g., bedrest) or diet modifications (e.g., fluids); and presenting the user with medical information, such as journal articles and the like.

The invention may also include a "virtual specialist" feature. This feature is useful for supporting the user with decisions and information pertaining to injuries or ailments that are beyond the scope of the user's judgment of assessment, diagnosis, or treatment. The feature may be based upon the experience, input, or predictive model of a separate user or a group of users. The feature may be accessed by user selection, or the Host Computer can automatically select and query a virtual consultant model based on data received from the user. The Host Computer may use rule-based or learning-based algorithms, in any of the manners described with reference FIG. 1, to determine when to access the virtual specialist feature and which virtual consultant is best to use. To supply the virtual specialist information, the Host Computer draws upon information that it retrieves and analyzes from its memory or from at least one Informational Computer, described with reference to FIG. 2 and FIG. 3.

When executing the virtual specialist feature, the Host Computer supplies the user with decisions and information that pertain to the specific ailment or injury and information regarding the probable actions or recommendations of a medical professional, or group of medical professionals, that specializes in a medical discipline that addresses the ailment or injury. For instance, a general medical practitioner who encounters a child suffering from poor blood circulation may not have the ability to immediately consult a pediatric surgeon or cardiologist. The invented system would provide a "virtual" specialist to meet the practitioner's needs, by dispensing information about what such a specialist would most likely do or recommend, allowing time until a real consultation could be had. The virtual specialist may also provide the user with information that allows "meantime care," which suggests actions that will maintain the patient in the best possible condition, until a specialist arrives for in-person consultation.

In one embodiment of the invention, the Host Computer receives input from one or more collections of different medical personnel, and develops a behavioral model for each collection. A user may then view predictions from collections of medical personnel, where each collection may comprise just one medical personnel, which may be the user or a medical personnel that is not the user, or a group of medical personnel that includes or does not include the user. Using the virtual specialist feature, the user can direct the Host Computer to provide information corresponding to the likely actions of "practitioner X or group Y," given the data that has been input about a patient to the Host Computer.

For example, X may be a specialist or even a hypothetical practitioner that is programmed to reflect standard protocol among practitioners of a certain type. Y may be a collection of specialists such as cardiologists, a collection of elite medical personnel such as the group of medical personnel at Johns Hopkins, or even a hypothetical group of medical professionals in general, that reflect standard protocol among medical personnel of a certain type. In this way, the virtual specialist feature may make suggestions from various perspectives. For instance, upon the user accessing the virtual specialist feature in regard to a specific patient, the Host Computer might, for example, output the most likely treatment or action to be rendered by medical personnel X, by group Y specialists, and the "standard choices" by the medical community. This would provide the user with the most choices in a very efficient manner.

The virtual specialist feature need not be limited only to medical specialists. In one embodiment of the virtual specialist feature, a general medical practitioner who wishes to improve the effectiveness of his documentation of medical encounters and of his coding or billing practices may not have billing or coding expertise. The invented system would provide a "virtual" specialist to meet the practitioner's needs, by predicting what an expert coding specialist would document at each phase of the encounter, by predicting questions an expert coder would ask to enhance the current documentation to increase reimbursement levels, or predicting the code an expert coder would select with regard to a particular patient encounter.

Figure 6:
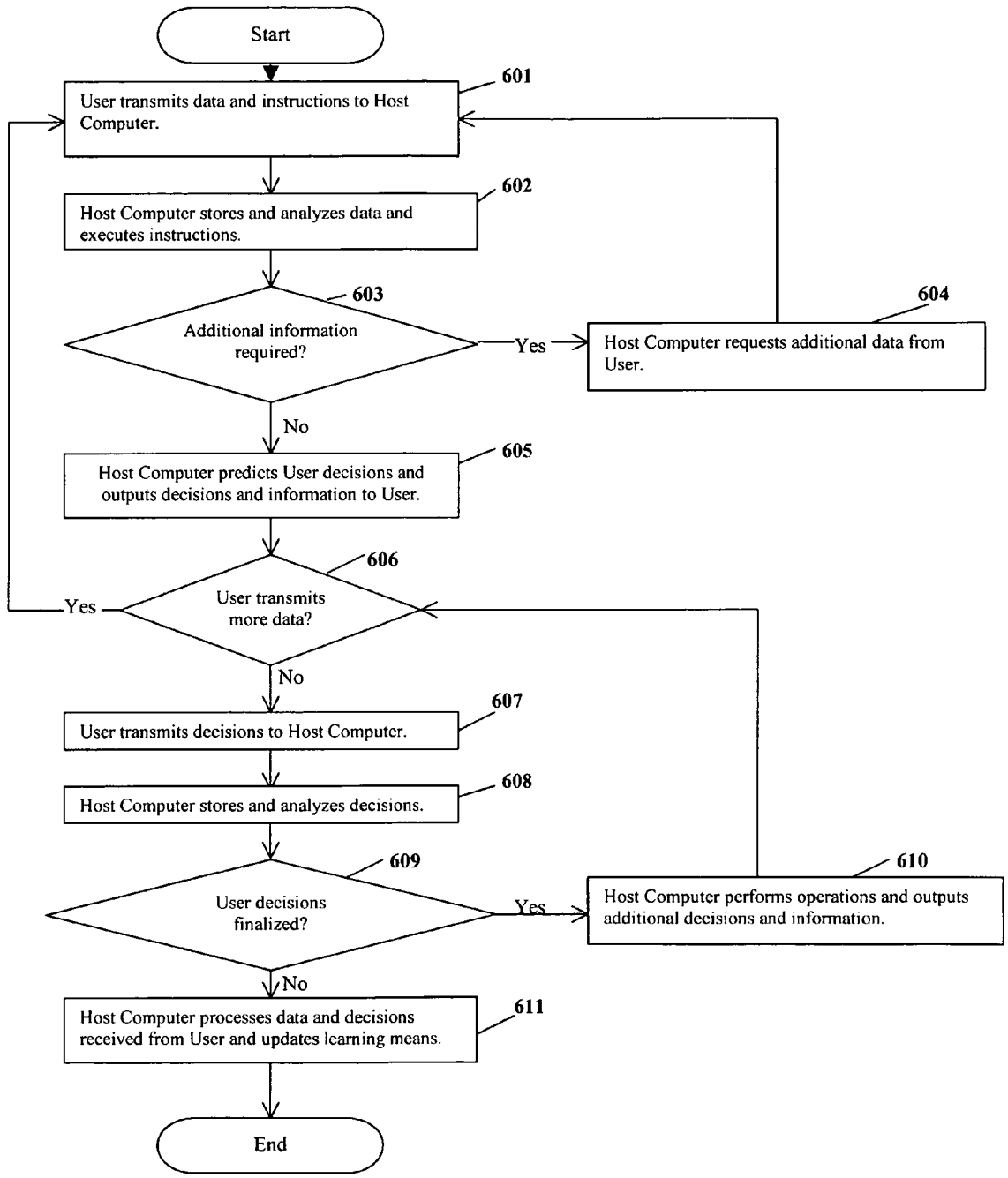
FIG. 6 shows a flow diagram, illustrating the steps and flow of the currently invented method.

Now referring to FIG. 6, the current invention is also directed to a method for providing adaptive medical decision support. In accordance with step 601, a user transmits data and instructions to the Host Computer. The data transmitted by the user comprises patient and clinical data, and may include any of the sorts of data that are exemplified in FIG. 4. The user may use the User Device to communicate with the Host Computer via a wireless communication link. The user may also use a General Use Device to communicate with the Host Computer, via global, wide area, or local area network technology. The user may communicate with the Host Computer across a graphical user interface, such as an electronic medical chart interface.

In accordance with step 602 the Host Computer stores and analyzes the data and executes the instructions that it receives. The Host Computer may store the data temporarily or permanently using its own memory means, or it may communicate the data to one or more Informational Computers for storage. In accordance with step 603, the Host Computer determines whether additional information is required or recommended and may request this information form the user in accordance with step 604. If such requests are made, the user may enter data and instructions, resulting in at least one additional iteration of steps 601–604.

In accordance with step 605 the Host Computer predicts the user's decisions from the data received and outputs these predicted decisions to the user. The Host Computer may also output information to the user that the Host Computer would obtain if the user had actually made each of the decisions. For example, if the data received from the user pertains to the patient's symptoms or medical problem, the Host Computer may predict and output potential diagnoses, but may also suggest further diagnostic actions, give warnings pertaining to particular diagnoses that merit further investigation of patient symptoms, provide journal articles and the like that discuss each potential diagnosis, and suggest treatment orders or courses of action. The Host Computer may retrieve information from its own memory means, for example from a database, or from at least one Informational Computer with which the Host Computer communicates. Alternatively, the Host Computer may output only the decisions that it predicts and await the user's instruction to retrieve pertinent information.

The Host Computer makes its predictions about a user's medical decisions in accordance with step 605, via a learning means that may execute behavioral models, rule-based algorithms, learning-based algorithms, neural networks, or a combination of these, in any of the manners described with reference to FIG. 1. Where a combination of rule-based algorithms and learning-based algorithms are used, the resulting information may be merged together, producing a single output, or the information of each type of algorithms may be kept separate and made selectable by the user.

The output from the Host Computer in step 605 may comprise decisions and information output from a virtual specialist feature. Such decisions and information may pertain to injuries or ailments that are beyond the scope of the user's judgment of assessment, diagnosis, or treatment, and may reflect the experience, decisions, or input of a separate user or a group of users. The feature may be accessed by user selection, or the Host Computer can automatically select and query a virtual consultant model based on data received from the user. The Host Computer may use rule-based or learning-based algorithms, in any of the manners described with reference FIG. 1, to determine when to access the virtual specialist feature and which virtual consultant is best to use. To supply the virtual specialist information, the Host Computer draws upon information that it retrieves and analyzes from its memory or from at least one Informational Computer, described with reference to FIG. 2 and FIG. 3.

When executing the virtual specialist feature, the Host Computer supplies the user with decisions and information that pertain to the specific ailment or injury and information regarding the probable actions or recommendations of a medical professional, or group of medical professionals, that specializes in a medical discipline that addresses the ailment or injury. For instance, a general medical practitioner who encounters a child suffering from poor blood circulation may not have the ability to immediately consult a pediatric surgeon or cardiologist. The present system would provide a "virtual" specialist to meet the practitioner's needs, by dispensing information about what such a specialist would most likely do or recommend, allowing time until an actual consultation could be made. The virtual specialist may also provide the user with information that allows "meantime care," which suggests actions that will maintain the patient in the best possible condition, until a specialist arrives for in-person consultation.

The virtual specialist feature need not be limited only to medical specialists. In one embodiment of the virtual specialist feature, a general medical practitioner who wishes to improve the effectiveness of his documentation of medical encounters and of his coding or billing practices may not have billing or coding expertise. The invented system would provide a "virtual" specialist to meet the practitioner's needs, by predicting what an expert coding specialist would document at each phase of the encounter, by predicting questions an expert coder would ask to enhance the current documentation to increase reimbursement levels, or predicting the code an expert coder would select with regard to a particular patient encounter.

In one embodiment of the invention, the Host Computer receives input from one or more collections of different medical personnel and develops a behavioral model for each collection. A user may then view predictions from collections of medical personnel, where each collection may comprise just one medical personnel, which may be the user or a medical personnel that is not the user, or a group of medical personnel that includes or does not include the user. Using the virtual specialist feature, the user can direct the Host Computer to provide information corresponding to the likely actions of "practitioner X or group Y," given the data that has been input about a patient to the Host Computer.

For example, X may be a specialist or even a hypothetical practitioner that is programmed to reflect standard protocol among practitioners of a certain type. Y may be a collection of specialists such as cardiologists, a collection of elite medical personnel such as the group of medical personnel at Johns Hopkins, or even a hypothetical group of medical professionals in general, that reflect standard protocol among medical personnel of a certain type. In this way, the virtual specialist feature may make suggestions from various perspectives. For instance, upon the user accessing the virtual specialist feature in regard to a specific patient, the Host Computer might, for example, output the most likely treatment or action to be rendered by medical personnel X, by group Y specialists, and the "standard choices" by the medical community. This would provide the user with the most choices in a very efficient manner.

In accordance with step 606, the user receives output from the Host Computer, which comprises the decisions predicted by the Host Computer, whether or not accompanied by additional pertinent information. The user may transmit more data to the Host Computer, in response to the output information that the user has received, resulting in an additional iteration of steps 601–606.

In accordance with step 607, the user transmits decisions to the Host Computer. The decisions transmitted by the user may be selected from among those decisions output to the user, or the user may input decisions that the Host Computer did not predict. The decisions input by the user may pertain, for example, to patient assessment, such as medical tests or physical examinations to be employed by the user. The decisions may pertain to diagnosis, such as the user's adjudged identification of a disease or injury. The decisions may pertain to treatment orders that are to be given by the user, including for example, specific procedures, types and brands of medication, or modifications in a patient's behavior or diet. The decisions may pertain to multiple aspects of patient care.

In accordance with step 608, the Host Computer stores and analyzes the decisions transmitted by the user. The Host Computer may store the decisions temporarily or permanently using its own memory means, or on one or more Informational Computers with which it communicates.

In accordance with step 609, it is determined whether the user's decisions are final. If not, then in accordance with step 610, the Host Computer may output to the user additional information, such as suggestions, alternatives, warnings, and/or highlights pertaining to the decision(s) received from the user, and new decisions and pertinent information as described previously. The user may then receive the output, resulting in an additional iteration of step 606. The user may transmit decisions to the Host Computer, in response to the output suggestions, alternatives, warnings, or highlights, resulting in an additional iteration of steps 607–609. Alternatively, the user may update or reenter data, prior to entering decisions, resulting in an additional iteration of steps 601–609.

In accordance with step 611, once the user's decisions have been made final, the Host Computer processes the data and decisions pertaining to a patient's case and may then enhance its predictive operations by updating its learning means. Where the Host Computer uses rule-based algorithms, it may customize its operations, by updating the rules. Where the Host Computer uses learning-based algorithms, such as a Bayesian network, inductive logic, or linear regression, in order to maintain a model a user's behavior and preferences, the Host Computer may update its operations by updating the model. Where the Host Computer employs neural networks at various decision nodes, as described with reference to FIG. 1, the Host Computer updates each neural network, after receiving data and actual decisions from the user.

In step 611, the user may be part of one or more groups that are being modeled. In such a case, the Host Computer processing the data and decisions pertaining to a patient's case, and updating its operations and predictive models, take place once the user's decisions have been made final.

The prediction process is thus adapted to the user, such that the Host Computer will predict the decisions actually input by a user in one case, when similar data or combinations of data are received in another case. But, the predictive process may also be updated, by predictively customizing the operations to user habits and preferences, while taking into account the characters of the user's specialty and patient populations. For instance, by updating its learning module with user habits, preferences, etc., the Host Computer can increase its ability predict when the user is likely to consult the virtual specialist feature of the invention, what medications the user prefers to prescribe for various ailments, what tests or diagnoses, if any, are commonly or uniformly rendered among the user's patient populations, etc. Thus, in addition to better predicting diagnoses and pertinent information, the Host Computer can tailor the details of all its operations to the user's habits and preferences.

Regardless of the algorithms or models employed by the learning means, the Host Computer may update the learning means each time that data or decisions are received from the user. Alternatively, updating may occur in "batch form," whereby updating occurs after a set period, such as after each case is complete, after a pre-defined number of cases are complete, after a pre-defined time period elapses, or after a pre-defined amount of data or decisions are received from the user, or any combination of these.

The present invention is also directed to a software program, embodied on a computer-readable medium, incorporating the present method, which has been described in full detail with reference to FIG. 6.

Figure 7:
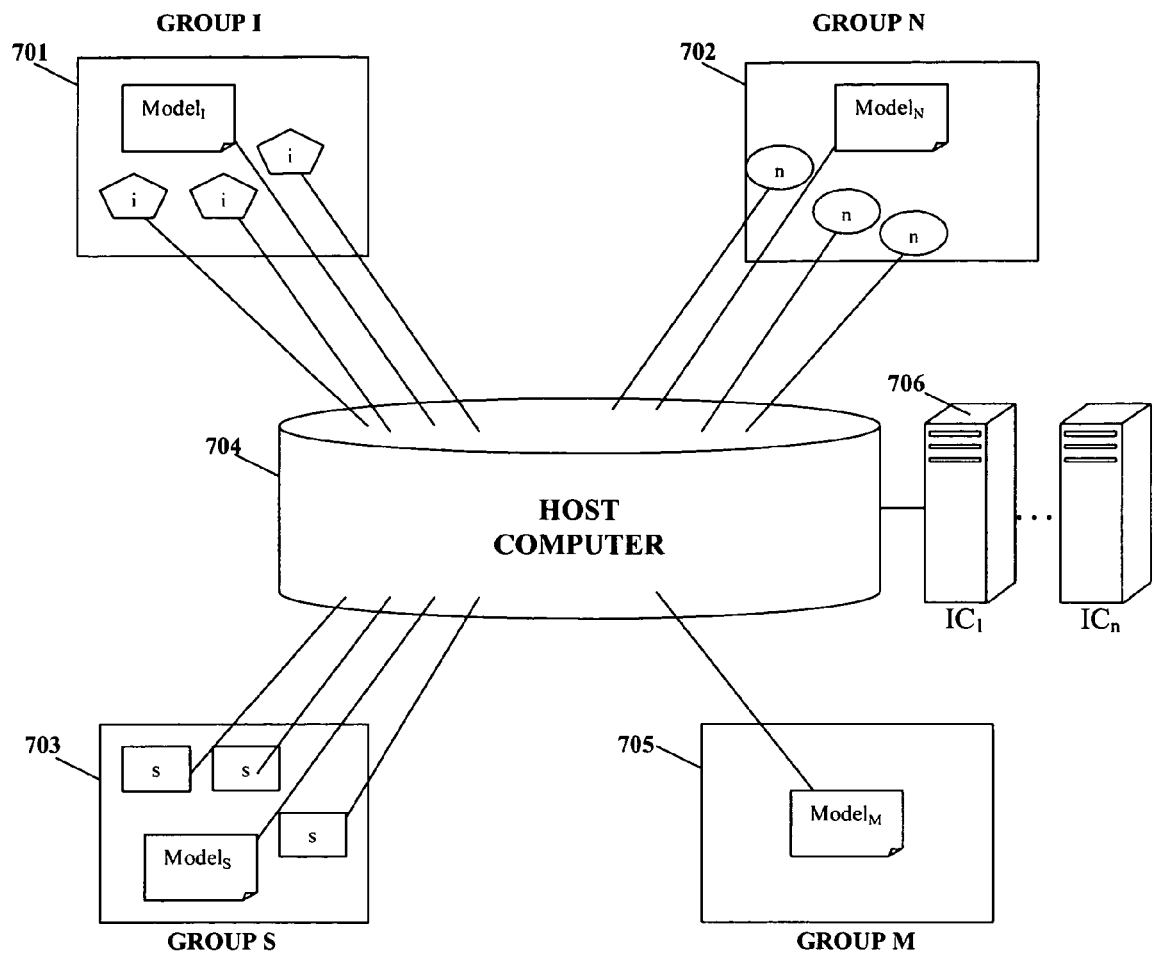
FIG. 7 shows a pictorial diagram, illustrating one embodiment for implementing the method shown in FIG. 6, in a multi-user environment.

FIG. 7 illustrates one embodiment for using the present system and method for adaptive decision support, when the system and method are implemented in a multi-user medical environment. In this embodiment, medical professionals are placed into groups that may include one or more members. The groups may be categorized by type of professional, such as nurses, surgeons, medical personnel, medical personnel assistants (P.A.s), medical students, etc. Groups may also be categorized by specialty or department, such as they might be in a hospital. In this case, medical professionals of any type (nurses, doctors, P.A.s, etc.) who work in one specialty or department would potentially fall into the same corresponding group. Groups may alternatively consist only of doctors who practice in one specialty, such as "cardiologists," with nurses, etc., falling into a nurse group or even a cardiology nurse group, for example. Groups may also consist of further specialized doctors, such as "all Johns Hopkins cardiologists," or "all Sarnoff fellows."

For example, a Group I 701 could consist of individual internists. Each internist communicates with the Host Computer 704, whether by a User Device or a General Use Device, as are described with reference to FIGS. 1 and 3. The Host Computer 704 implements the invented method described with reference to FIG. 6. Data, decisions, and information that are stored on the Host Computer 704, or on the Informational Computers 706 with which the Host Computer 704 communicates, are separated into a grouping that corresponds to the Group I 701. The Host Computer 704 customizes its operations and predictions to suit each specific internist, in accordance with the invented method, and may create an overall model of the behavior, preferences, patient populations, or medical specialties of the Group I 701. Alternatively, the Group I 701 may devise its own model and communicate it to the Host Computer 704 as a Model$_I$. A Group N 702 and a Group S 703 interact with the Host Computer 704 in the same fashions as described for the Group I 701.

In one embodiment of the invention, the step of updating individual and group models may be slightly altered to provide for the status of individual users. In this embodiment, only certain users' input will be used by the invention to update individual or group models that are used to implement the predictive capabilities of the invention. As a corollary, some users' models may be updated based not on their input, but upon the input of other users. For instance, the Group I 701 in FIG. 7 may include both resident doctors at a hospital, in addition to interns who have only recently begun practicing. Thus, the system operators may elect for only the resident doctors' input and decisions to be used to update the Model$_I$ and, they may select only the input and decisions of the resident doctors to be used in updating the internists' individual predictive models also.

As an extension of this embodiment, suppose the Group S 703 consists of medical students. The system operators may select only for certain doctors' input and decisions to be used to update both the Model$_s$ and the individual predictive models for each student, even though the doctors may be placed in an entirely different group. The same could apply for the Group N 702, for example, if the group consisted of nurses. Alternatively, system operators may allow for individual users to update their own predictive models, but for only certain users' input and decisions to update group models, thereby allowing for other users to evaluate their progress in learning the practice of medicine or a certain field of medicine.

The Group M 705 can represent groups that transmit external or standardized models to the Host Computer 704, which are not developed by the Host Computer 704 from processing the actions of individuals within the environment. For example, models for certain types of care that are not extensively served by a certain hospital, such as trauma, can be communicated to the Host Computer 704 from sources external to the hospital. These models may be the result of standard medical practices, protocols established by those who manage the environment, such as a hospital protocol, protocols developed from evidence-based medicine, protocols developed by a payor, protocols provided by a pharmacy benefits management company, protocols developed by a pharmaceutical company, or protocols developed by business managers, including billing and coding specialists. Alternatively, they may be developed by elite groups of medical personnel, such as medical schools or teaching hospitals. In these cases, only the Model$_M$ is communicated to the Host Computer by the Group M 705. The Group M 705 may comprise the creators of the model and/or those within the medical environment that implements the current invention. System operators may elect for the external models to comprise the individual or group models for certain users, in accordance with the embodiments described above.

As a result of the embodiment illustrated in FIG. 7, the Host Computer 704 may provide the "virtual specialist" feature of the current invention, as described with reference to FIGS. 5 and 6, by allowing users from different groups to access the continually developing models and data of other groups of users, models of individual users, and models placed on the Host Computer 704 by groups such as the Group M 705. This can result in the capacity for users to receive virtual second opinions, for example, by accessing the models of other groups, or of individual users, such as managing medical personnel.

Figure 8:
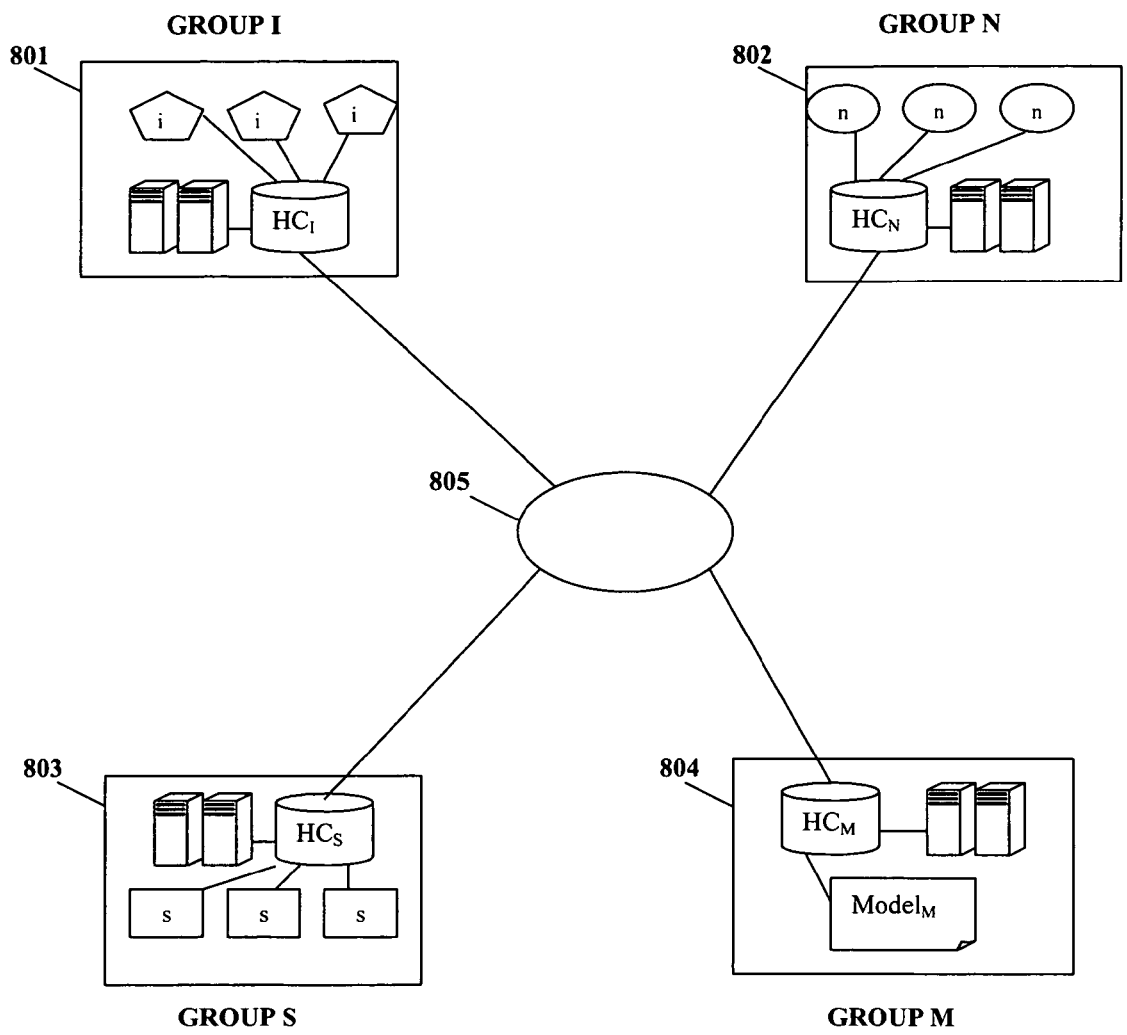
FIG. 8 shows a pictorial diagram, illustrating an alternative embodiment for implementing the method shown in FIG. 6, in a multi-user environment.

FIG. 8 illustrates another embodiment for using the invented system and method for adaptive decision support, when the system and method are implemented in a multi-user medical environment. In this embodiment, medical professionals are placed into groups, in any of the manners described with reference to FIG. 7. However, the users of each group communicates directly with one iteration of the invented system. For example, each of the users in the Group I 801 communicates with the Host Computer HC$_I$, whether by a User Device or a General Use Device, described in reference to FIGS. 1–3. HC$_I$ implements the invented method described with reference to FIG. 6. Data, decisions, and information for each user in the Group I 801 and corresponding models is stored on HC$_I$ or on the Informational Computers with which HC$_I$ communicates. HC$_I$ customizes its operations to suit each specific user in the Group I 801, in accordance with the invented method, and may create an overall model of the behavior, preferences, patient populations, or medical specialties of the Group I. A Group N 802 and a Group S 803 interact with the Host Computers HC$_N$ and HC$_S$, respectively, each of which also implements the method described with reference to FIG. 6, in the same fashions as the Group I interacts with HC$_I$.

In one embodiment of the invention, the step of updating individual and group models may be slightly altered to provide for the status of individual users. In this embodiment, only certain users' input will be used by the invention to update individual or group models that are used to implement the predictive capabilities of the invention. As a corollary, some users' models may be updated based not on their input, but upon the input of other users. For instance, the Group I 801 in FIG. 8 may include both resident doctors at a hospital, in addition to interns who have only recently begun practicing. Thus, the system operators may elect for only the resident doctors' input and decisions to be used to update the Model$_I$; and, they may select only the input and decisions of the resident doctors to be used in updating the internists' individual predictive models also.

As an extension of this embodiment, suppose the Group S 803 consists of medical students. The system operators may select only for certain doctors' input and decisions to be used to update both the Models and the individual predictive models for each student, even though the doctors may be placed in an entirely different group. The same could apply for the Group N 802, for example, if the group consisted of nurses. Alternatively, system operators may allow for individual users to update their own predictive models, but for only certain users' input and decisions to update group models, thereby allowing for other users to evaluate their progress in learning the practice of medicine or a certain field of medicine.

The Group M 804 can represent groups that transmit external or standardized models to The Host Computer, such as those described with reference to FIG. 7. In these cases, only the Model$_M$ is communicated to the Host Computer HC$_M$ by the Group M 804. The Group M may comprise the creators of the model and/or those within the medical environment that implements the current invention. The separate Host Computers HC$_I$, HC$_N$, HC$_S$, and HC$_M$, communicate with each other directly or via a Hub 805. The Hub 805 may comprise a switching device or a computing device, such as a server computer. Communication among the Host Computers may take place by any suitable means for computing devices to communicate remotely with each other. Examples include global, wide area, and local area networks. System operators may elect for the external models to comprise the individual or group models for certain users, in accordance with the embodiments described above.

As a result of the embodiment illustrated in FIG. 8, each Host Computer may provide the "virtual specialist" feature of the current invention, described with reference to FIGS. 5 and 6, by allowing users from different groups to access the continually developing models and data of other groups of users, models of individual users, and models placed on the system by groups such as the Group M 804. This can result in the capacity for users to receive virtual second opinions, for example, by accessing the models of other groups, or by individual users, such as managing medical personnel.

FIG. 9 illustrates an example of the electronic medical chart graphical user interface 900 that may be used in conjunction with one embodiment of the current invention, described with reference to an embodiment of the system shown in FIGS. 1–3. In this example embodiment of the GUI, various categories of information are selectable from tabs 901 labeled with the informational categories. Example categories may include Patients, Schedule, Health Plans, and the like. When a tab 901 is selected, a user may enter or choose information within an informational region 902. When information is chosen, such as a particular patient listed under the Patients tab, subcategories of information 903 are selectable by the user. The subcategories 903 (exemplified first by HPI—History of Present Illness) provide certain types of information within the informational region that are all specific to, for example, the chosen patient. The information shown may include any data and data fields suitable to provide the user with information about the chosen information, including any of the information exemplified in FIG. 4, but also including user-directed information, such as information about individual correspondence, schedules, messages, forms, other administrative tasks, narratives, etc. The GUI may also provide a login/logout feature and may show the user's name, as exemplified at 904.

Figure 10:
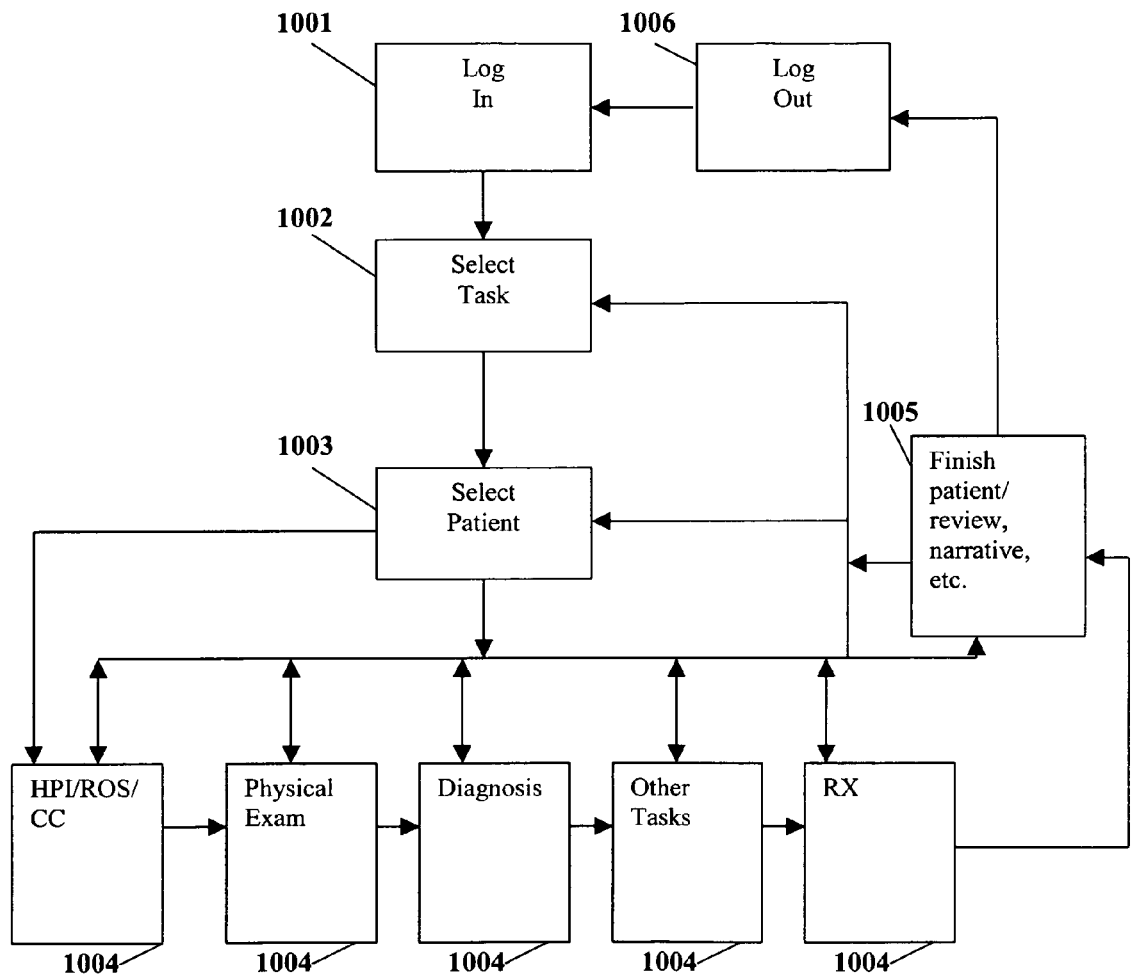
FIG. 10 is a flow diagram illustrating an embodiment of the steps, in which a user may interact with the currently invented systems and methods.

FIG. 10 shows a flow diagram, which illustrates how the present systems and methods described above may be applied by a user. In accordance with step 1001, the user logs into the system. The user may login via a portable computing device, or a general use device. In one embodiment, the user logs in, using a portable computing device that is provided with an electronic medical chart GUI. In accordance with step 1002, the user may next select the task to be performed, such as entering new data, updating data, or reviewing data. In accordance with step 1003, the user then selects the patient for whom the task will be performed, which may include selecting an existing patient or opting to begin a new patient record. The user may then enter, update, review, etc., data for any of a plurality of tasks 1004, such as preliminary patient information, physical examination and assessment, diagnosis, treatment orders, etc. During each task 1004, the invented method described with reference to FIG. 6 is executed. This allows for each task 1004 to be performed and ended directly after patient selection, without proceeding to the other tasks. It also allows for the tasks 1004 to be performed consecutively, for example, with new patients. Once a task 1004 is completed, the user may select a new patient or a new task 1004, or the user may proceed to a finishing step 1005. The finishing step 1005 allows the user to review the results of the session and to complete administrative tasks, such as submitting narratives, changing scheduling, drafting correspondence, and the like. After the finishing step 1005, the user may proceed to another patient or task, or log out of the system at step 1006.

Figure 11:
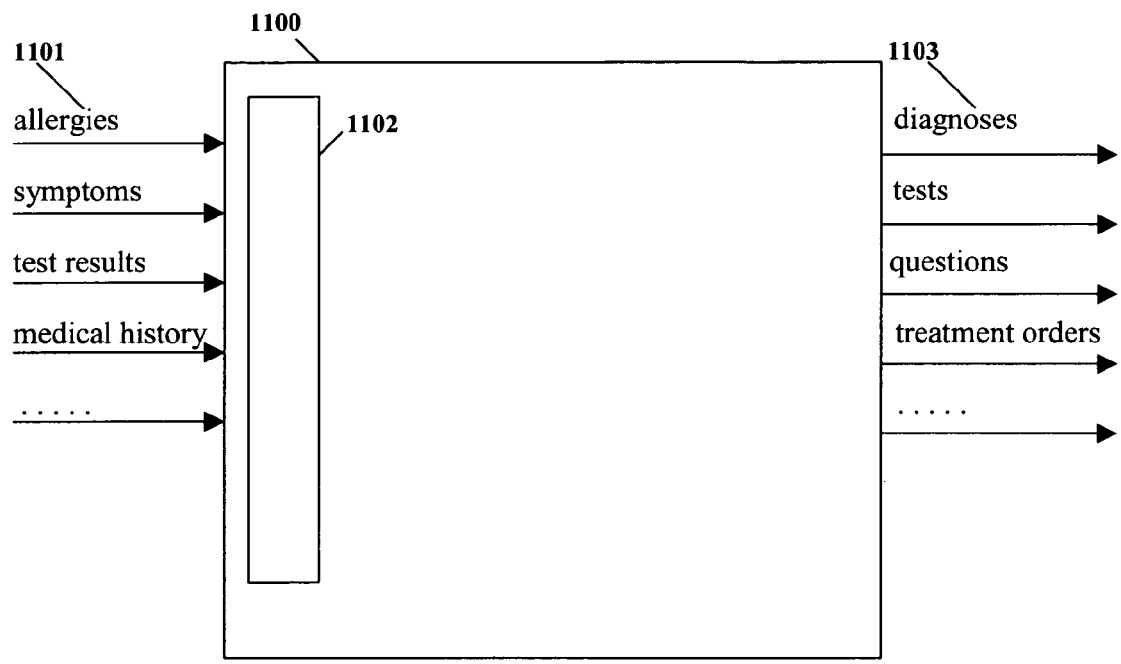
FIG. 11 illustrates an example implementation of a learning-based model, in accordance with the current invention.

FIG. 11 describes an exemplary implementation of a learning-based model for a user at a decision point implemented via neural networks. FIG. 11 displays a learning model 1100 that receives examples of input data 1101, which comprise findings about a current patient, such as allergies, symptoms, test results, medical history, etc. In general, these are data that the medical professional considers in making a medical decision in regard to the patient. FIG. 11 displays example outputs 1103, which comprise the potential medical decisions that the medical professional may make, such as diagnoses, diagnostic tests, questions, or treatment orders. Each input variable 1101 is represented as one unit at the input layer 1102, and is assigned an activation value. The activation value may comprise, for example, a numerical scale, such as a 0/1 decision, with missing values represented by e.g. 0.5. In the output 1103, the activation of each unit represents the a posteriori probability that the choice is correct, given the training data. Thus, the system indicates what the best choices are and how confident it is in each of them. The network is trained with backpropagation based on the actual cases of inputs and decisions collected by the system. Standard methods of crossvalidation can be used to decide when to stop training. Different training sets are constructed to model different physicians or groups of physicians. Periodically, as new data come in, the networks can be further trained with the more comprehensive data set to improve accuracy and coverage of different cases.

Figure 12:
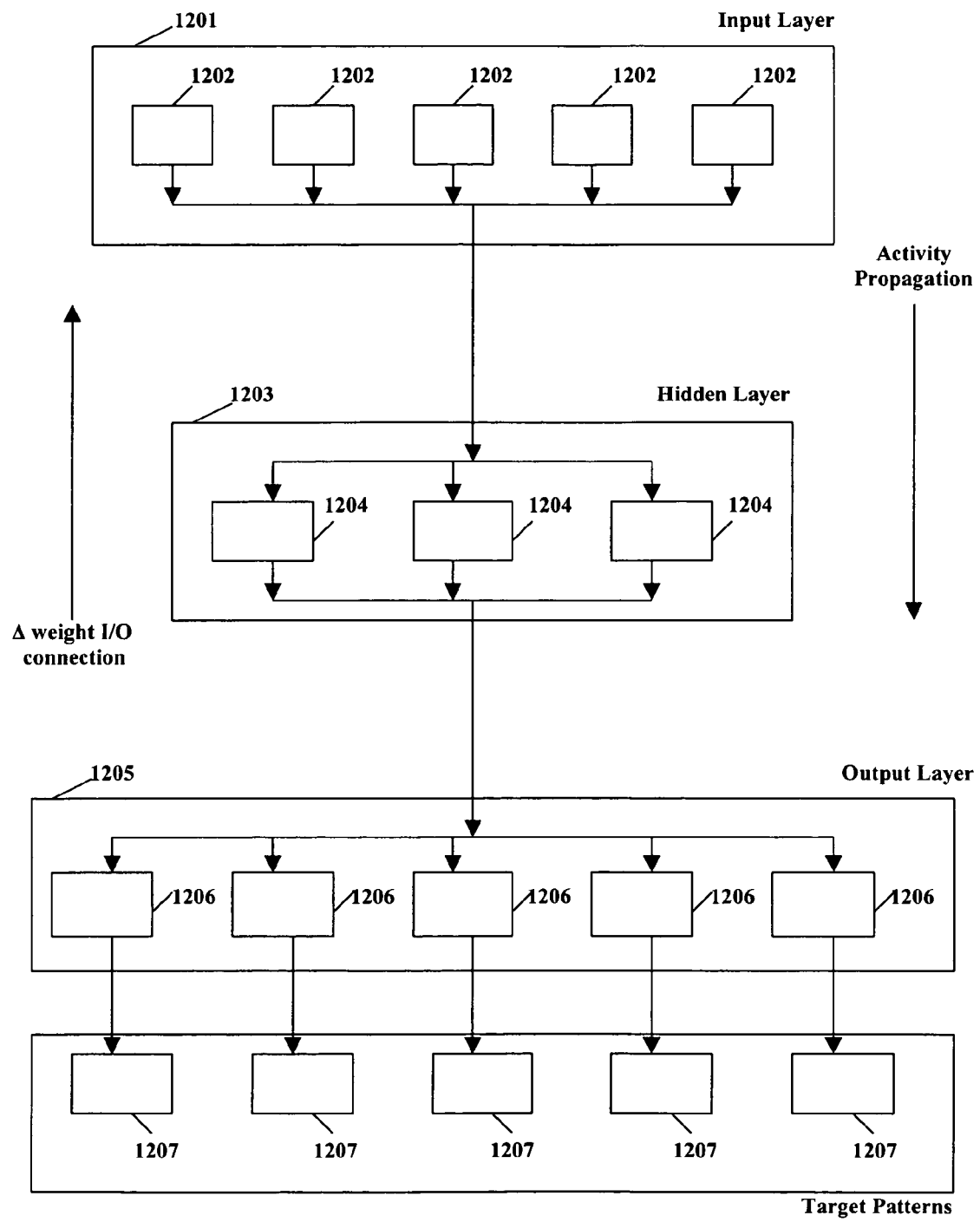
FIG. 12 illustrates an example implementation of a neural networks system.

A neural network based learning system may be implemented using standard techniques, such as that illustrated in FIG. 12. This exemplary neural networks system consists of an input layer 1201, having input units 1202; a hidden layer 1203, having hidden units, 1204; and an output layer 1205, having output units 1206; and target patterns 1207. The input layer 1201 is connected to the hidden layer 1203 by input connections that connect any one of the input units 1202 to any one of the hidden units 1204. Similarly, the hidden layer 1203 is connected to the output layer 1205 by output connections that connect any one of the hidden units 1204 to any one of the output units 1206.

The values of input variables are used to activate the input units 1202. Each hidden unit 1204 computes a weighted sum of the input unit activations. The sums are weighted by the connection weights, which increase as one moves from the output connections to the input connections. The hidden unit 1204 then outputs an activation that's a nonlinear, continuous function (such as a sigmoid or a Gaussian) of the sum. Analogously, each output layer unit 1206 computes the weighted sum of the hidden layer activations, and generates a nonlinear function of the sum as its output. The output activations are then interpreted as values of output variables.

The network is trained by providing target patterns 1207, which are correct values for the output units, with regard to each input variable. The weights of the network are then changed using, for example, a backpropagation training procedure. An error signal for each output unit 1206 is formed as a difference between the output unit 1206 and the target patterns 1207. A gradient of the error signal with regard to the network weight values is computed, and weights are changed a small step along the gradient. After the input variables and target patterns are shown several times and weights changed this way, the weights converge to values such that the network generates the correct output values for each input variable. The network will also compute the correct outputs for new examples by nonlinearly interpolating between the examples in the training set of input variables.

Using the foregoing, the invention may be implemented using standard programming or engineering techniques including computer programming software, firmware, hardware or any combination or subset thereof. Any such resulting program, having a computer readable program code means, may be embodied or provided within one or more computer readable or usable media, thereby making a computer program product, i.e. an article of manufacture, according to the invention. The computer readable media may be, for instance a fixed (hard) drive, disk, diskette, optical disk, magnetic tape, semiconductor memory such as read-only memory (ROM), or any transmitting/receiving medium such as the Internet or other communication network or link. The article of manufacture containing the computer programming code may be made and/or used by executing the code directly from one medium, by copying the code from one medium to another medium, or by transmitting the code over a network.

An apparatus for making, using or selling the invention may be one or more processing systems including, but not limited to, a central processing unit (CPU), memory, storage devices, communication links, communication devices, server, I/O devices, or any sub-components or individual parts of one or more processing systems, including software, firmware, hardware or any combination or subset thereof, which embody the invention as set forth in the claims.

User input may be received from the keyboard, mouse, pen, voice, touch screen, or any other means by which a human can input data to a computer, including through other programs such as application programs.

The descriptions of FIGS. 1–12 are provided for illustrative purposes only, and are not meant to be limiting to the overall invention. Although the present invention has been described in detail with reference to certain embodiments, it should be apparent that modifications and adaptations to those embodiments may occur to persons skilled in the art without departing from the spirit and scope of the present invention as set forth in the following claims.

What is claimed is:

1. A computer-implemented method for adaptively supporting medical decisions of at least one user, comprising:
   a. receiving data at a host computer from a graphical medical record interface associated with a medical workflow, the graphical medical record interface implemented on a wireless portable interface device;
   b. predicting at least one medical decision at the host computer based on the received data;
   c. displaying the at least one predicted medical decision in the graphical medical record interface implemented on the wireless portable interface device;
   d. receiving at least one user-decision from the at least one user via the graphical medical record interface; and
   e. learning to predict the at least one user-decision using the host computer based on the received data and the at least one user-decision.

2. The method of claim 1, wherein the step of receiving data further comprises receiving data via a wireless communication means.

3. The method of claim 2, wherein the wireless communication means is chosen from a group consisting of infrared signals, radio signals, and pulse codes.

4. The method of claim 1, wherein the step of learning further comprises updating at least one learning module chosen from a group consisting of behavioral models, rule-based algorithms, learning-based algorithms, and neural networks.

5. The method of claim 1, wherein the step of learning further comprises customizing a plurality of operations to at least one parameter chosen from a group consisting of preferences of a user, habits of a user, medical specialties of a user, patient populations of a user, preferences of a group of users, habits of a group of users, medical specialties of a group of users, and patient populations of a group of users.

6. The method of claim 1, further comprising the step of executing the at least one user-decision, after the step of receiving the at least one user-decision.

7. The method of claim 1, further comprising executing the at least one predicted medical decision, before the step of receiving the at least one user-decision.

8. The method of claim 1, wherein the graphical medical record interface includes an electronic medical chart graphical user interface.

9. A software program, embodied on a computer-readable medium, incorporating the method recited in claim 1.

10. A method for adaptively supporting medical decisions of at least one user, comprising:
   a. receiving data at a host computer from a graphical interface implemented on an interface device;
   b. transmitting the data to at least one neural network;
   c. predicting at least one medical decision, via the at least one neural network based on the received data;
   d. displaying the at least one predicted medical decision in the graphical interface implement on the interface device;
   e. receiving at least one user-decision from the at least one user via the graphical interface implemented on the interface device;
   g. learning to predict the at least one user-decision at the host computer based on the received data and the at least one user-decision; and
   h. wherein learning comprises updating the at least one neural network.

11. The method of claim 10, wherein the step of receiving data further comprises receiving data via a wireless communication means.

12. The method of claim 11, wherein the wireless communication means is chosen from a group consisting of infrared signals, radio signals, and pulse codes.

13. The method of claim 10, wherein the step of learning further comprises customizing a plurality of operations to at least one parameter chosen from a group consisting of preferences of a user, habits of a user, medical specialties of a user, patient populations of a user, preferences of a group of users, habits of a group of users, medical specialties of a group of users, and patient populations of a group of users.

14. The method of claim 10, further comprising the step of executing the at least one user-decision, after the step of receiving the at least one user-decision.

15. The method of claim 10, further comprising executing the at least one predicted medical decision, before the step of receiving the at least one user-decision.

16. The method of claim 10, wherein the graphical interface implemented on the interface device includes an electronic medical chart graphical user interface.

17. A software program, embodied on a computer-readable medium, incorporating the method recited in claim 10.

18. A computer-implemented method for adaptively supporting medical decisions of at least one user, comprising
   a. receiving at least one first quantity of computer readable data associated with a medical workflow;

b. receiving at least one user-decision associated with the medical workflow from a first at least one user via a graphical medical records interface;
c. learning to predict the at least one received user-decision based on the at least one first quantity of computer readable data and the at least one user-decision by adapting a computer implemented prediction model;
d. receiving at least one second quantity of computer readable data associated with the medical workflow;
e. predicting at least one medical decision based on the at least one second quantity of computer readable data using the computer implemented prediction model, the at least one medical decision being associated with the medical workflow;
f. displaying the at least one predicted medical decision via the graphical medical records interface; and
g. receiving at least one second user-decision associated with the medical workflow via the graphical medical records interface.

19. The method of claim 18, wherein the step of receiving the at least one second quantity of computer readable data further comprises receiving data via a wireless communication means.

20. The method of claim 19, wherein the wireless communication means is chosen from a group consisting of infrared signals, radio signals, and pulse codes.

21. The method of claim 18, wherein the step of learning further comprises updating at least one learning module chosen from a group consisting of behavioral models, rule-based algorithms, learning-based algorithms, and neural networks.

22. The method of claim 18, wherein the step of learning further comprises customizing a plurality of operations to at least one parameter chosen from a group consisting of preferences of a user, habits of a user, medical specialties of a user, patient populations of a user, preferences of a group of users, habits of a group of users, medical specialties of a group of users, and patient populations of a group of users.

23. The method of claim 18, wherein the method is implemented on at least one portable computing device.

24. The method of claim 18, wherein
the method is implemented on a host computer;
the host computer receives data from at least one portable computing device; and
the at least one portable computing device receives and displays output from the host computer.

25. The method of claim 18, further comprising the step of executing the at least one user-decision, after the step of receiving the at least one user-decision.

26. The method of claim 18, further comprising automatically executing the at least one predicted medical decision, before the step of receiving the at least one user-decision.

27. The method of claim 18, wherein the first at least one user comprises a specialist in a field of medicine.

28. The method of claim 18, wherein the first at least one user comprises a billing specialist or a coding specialist.

29. A software program, embodied on a computer-readable medium, incorporating the method recited in claim 18.

30. A computer-implemented method for adaptively supporting medical decisions, comprising
a. receiving a first quantity of computer readable data associated with a medical workflow;
b. predicting a first at least one medical decision associated with the medical workflow based on the computer readable data, via at least one rule-based algorithm;
c. displaying the first at least one medical decision in a graphical medical interface;
d. receiving at least one user-decision associated with the medical workflow from a first at least one user via the graphical medical interface;
e. learning to predict the at least one user-decision based on the at least one user-decisions and the computer readable data, wherein learning to predict the at least one user-decisions includes adapting the at least one rule-based algorithm;
f. receiving a second quantity of computer readable data associated with the medical workflow via the graphical medical interface; and
g. predicting, via at least one learning-based algorithm, a second at least one medical decision associated with the medical workflow based on the second quantity of computer readable data.

31. The method of claim 30, further comprising displaying the second at least one medical decision.

32. The method of claim 30, wherein the step of receiving the second quantity of computer readable data further comprises receiving the second quantity of computer readable data via a wireless communication means.

33. The method of claim 32, wherein the wireless communication means is chosen from a group consisting of infrared signals, radio signals, and pulse codes.

34. The method of claim 30, wherein the method is implemented on at least one portable computing device.

35. The method of claim 30, wherein
the method is implemented on a host computer,
the host computer receives data from at least one portable computing device; and
the at least one portable computing device receives and displays output from the host computer.

36. The method of claim 30, further comprising executing the first at least one medical decision, before the step of receiving the at least one user-decision.

37. The method of claim 30, further comprising the step of receiving a second at least one user-decision, after the step of predicting the second at least one medical decision.

38. The method of claim 37, further comprising the step of executing the second at least one user-decision, after the step of receiving the second at least one user-decision.

39. The method of claim 30, wherein the step of learning further comprises updating at least one learning module chosen from a group consisting of behavioral models, rule-based algorithms, learning-based algorithms, and neural networks.

40. The method of claim 30, wherein the step of learning further comprises customizing a plurality of operations to at least one parameter chosen from a group consisting of preferences of a user, habits of a user, medical specialties of a user, patient populations of a user, preferences of a group of users, habits of a group of users, medical specialties of a group of users, and patient populations of a group of users.

41. The method of claim 30, further comprising
a. predicting, via the at least one rule-based algorithm, a third at least one medical decision; and
b. displaying at least one predicted medical decision, chosen from a group consisting of the second at least one medical decision, the third at least one medical decision, and both the second and third at least one medical decisions.

42. The method of claim 41, further comprising executing the predicted medical decision chosen from the group consisting of the second at least one medical decision, the third at least one medical decision, and both the second and third at least one medical decisions.

43. The method of claim 41, wherein the predicted medical decision chosen from the group consisting of the second at least one medical decision, the third at least one medical decision is selected by at least one user, and both the second and third at least one medical decisions, is selected by at least one user.

44. The method of claim 41, wherein the predicted medical decision chosen from the group consisting of the second at least one medical decision, the third at least one medical decision, and both the second and third at least one medical decisions, is selected by a computing device.

45. The method of claim 41, further comprising the step of receiving a second at least one user-decision, after the step of predicting the third at least one medical decision.

46. The method of claim 45, further comprising the step of executing the second at least one user-decision after the step of receiving the second at least one user-decision.

47. The method of claim 45, further comprising learning to predict the second user-decision from the second quantity of data received.

48. The method of claim 47, wherein the step of learning further comprises updating at least one learning module chosen from a group consisting of behavioral models, rule-based algorithms, learning-based algorithms, and neural networks.

49. The method of claim 47, wherein the step of learning further comprises customizing a plurality of operations to at least one parameter chosen from a group consisting of preferences of a user, habits of a user, medical specialties of a user, patient populations of a user, preferences of a group of users, habits of a group of users, medical specialties of a group of users, and patient populations of a group of users.

50. The method of claim 30, further comprising displaying an electronic medical chart graphical user interface.

51. The method of claim 30, wherein the first at least one user comprises a specialist in a field of medicine.

52. The method of claim 30, wherein the first at least one user comprises a billing specialist or a coding specialist.

53. A software program, embodied on a computer-readable medium, incorporating the method recited in claim 30.

* * * * *